(12) United States Patent
Igawa et al.

(10) Patent No.: US 11,940,704 B2
(45) Date of Patent: Mar. 26, 2024

(54) ORGANIC COMPOUND, AND ELECTROCHROMIC ELEMENT, OPTICAL FILTER, IMAGE PICKUP APPARATUS, WINDOW, AND ELECTROCHROMIC MIRROR CONTAINING THE SAME

(71) Applicant: CANON KABUSHIKI KAISHA, Tokyo (JP)

(72) Inventors: Satoshi Igawa, Kanagawa (JP); Kenji Yamada, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 680 days.

(21) Appl. No.: 17/129,068

(22) Filed: Dec. 21, 2020

(65) Prior Publication Data

US 2021/0109415 A1 Apr. 15, 2021

Related U.S. Application Data

(63) Continuation of application No. PCT/JP2019/023738, filed on Jun. 14, 2019.

(30) Foreign Application Priority Data

Jun. 28, 2018 (JP) .................................. 2018-123695
Mar. 15, 2019 (JP) .................................. 2019-048986
Apr. 25, 2019 (JP) .................................. 2019-084741

(51) Int. Cl.
*G02F 1/1516* (2019.01)
*C07D 401/10* (2006.01)
(Continued)

(52) U.S. Cl.
CPC ......... *G02F 1/1516* (2019.01); *C07D 401/10* (2013.01); *C07D 471/04* (2013.01);
(Continued)

(58) Field of Classification Search
CPC ............... G02F 1/1516; G02F 2203/01; G02F 2203/02; G02F 2203/055; C09K 9/02;
(Continued)

(56) References Cited

U.S. PATENT DOCUMENTS 5,436,316 A * 7/1995 Yamamoto ......... C08G 73/0627
528/422
5,698,559 A * 12/1997 Wilkerson ........... C07D 213/30
544/405

(Continued)

FOREIGN PATENT DOCUMENTS

JP S62-135474 A 6/1987
JP 2007-171781 A 7/2007
(Continued)

*Primary Examiner* — Jane L Stanley
(74) *Attorney, Agent, or Firm* — Canon U.S.A., Inc., IP Division

(57) ABSTRACT

The present disclosure provides an organic compound represented by the following general formula [1]:

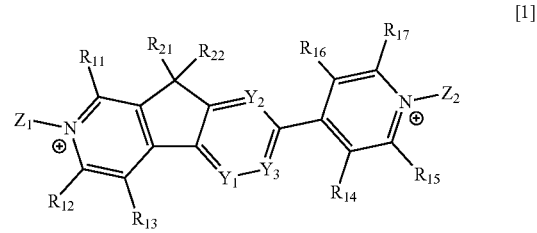

where $Z_1$ and $Z_2$ are each independently selected from an alkyl group that may have a substituent, an aryl group that may have a substituent, and an aralkyl group that may have a substituent; $R_{11}$ to $R_{17}$, $R_{21}$, and $R_{22}$ are each independently selected from a hydrogen atom and (Continued)

a substituent; $Y_1$ to $Y_3$ are each independently selected from a carbon atom, a N atom, and $(N^+\text{-}L)(X^-)$; and L is any one of an alkyl group, an aryl group, and an aralkyl group.

22 Claims, 5 Drawing Sheets

(51) Int. Cl.
<br>    *C07D 471/04*         (2006.01)
<br>    *C09K 9/02*           (2006.01)
<br>    *E06B 3/67*           (2006.01)
<br>    *E06B 9/24*           (2006.01)

(52) U.S. Cl.
<br>    CPC .............. *C09K 9/02* (2013.01); *E06B 3/6722* (2013.01); *E06B 9/24* (2013.01); *E06B 2009/2464* (2013.01); *G02F 2203/01* (2013.01); *G02F 2203/02* (2013.01); *G02F 2203/055* (2013.01)

(58) Field of Classification Search
<br>    CPC ... C07D 401/10; C07D 471/04; E06B 3/6722; E06B 9/24; E06B 2009/2464
<br>    See application file for complete search history.

(56) References Cited

U.S. PATENT DOCUMENTS

| | | | | |
|---|---|---|---|---|
| 9,701,671 | B2 * | 7/2017 | Igawa | ..................... G02F 1/163 |
| 10,527,905 | B2 * | 1/2020 | Kaneko | ............... G02F 1/13439 |
| 2003/0206326 | A1 * | 11/2003 | Berneth | ................... C09K 9/02 |
| | | | | 359/265 |
| 2017/0329195 | A1 * | 11/2017 | Igawa | ................. C07F 9/65583 |
| 2018/0113366 | A1 * | 4/2018 | Kaneko | ................ G02F 1/155 |
| 2018/0194995 | A1 * | 7/2018 | Archambeau | ........ C07D 213/22 |
| 2018/0237393 | A1 * | 8/2018 | Tamura | ................ C07D 213/06 |
| 2019/0002758 | A1 * | 1/2019 | Igawa | .................. E06B 3/6722 |
| 2020/0004095 | A1 * | 1/2020 | Yamada | .................. C09K 9/02 |
| 2021/0191217 | A1 * | 6/2021 | Yamada | ............... C07D 471/04 |

FOREIGN PATENT DOCUMENTS

| | | | | |
|---|---|---|---|---|
| JP | | 2017-197477 A | 11/2017 | |
| JP | | 2017-203001 A | 11/2017 | |
| JP | | 2018-024624 A | 2/2018 | |
| WO | | 2016/147543 A1 | 9/2016 | |
| WO | WO | 2016203700 A1 * | 12/2016 | ........... C07D 471/04 |
| WO | | 2017/005824 A1 | 1/2017 | |
| WO | | 2017/154681 A1 | 9/2017 | |

* cited by examiner

ORGANIC COMPOUND, AND ELECTROCHROMIC ELEMENT, OPTICAL FILTER, IMAGE PICKUP APPARATUS, WINDOW, AND ELECTROCHROMIC MIRROR CONTAINING THE SAME

CROSS-REFERENCE TO RELATED APPLICATIONS

This application is a Continuation of International Patent Application No. PCT/JP2019/023738, filed Jun. 14, 2019, which claims the benefit of Japanese Patent Application No. 2018-123695 filed Jun. 28, 2018, Japanese Patent Application No. 2019-048986 filed Mar. 15, 2019, and Japanese Patent Application No. 2019-084741 filed Apr. 25, 2019, which are hereby incorporated by reference herein in their entirety.

BACKGROUND OF THE INVENTION

Field of the Invention

The present invention relates to an electrochromic organic compound, and an electrochromic element, an optical filter, a lens unit, an image pickup apparatus, and a window that contain the electrochromic organic compound.

Background Art

As electrochromic (hereafter, may be abbreviated as "EC") materials, which undergo an electrochemical oxidation-reduction reaction to have different optical absorption properties (the coloration state and light transmittance), there are various known materials such as inorganic materials, organic polymer materials, and organic low-molecular-weight materials.

As representative examples of organic low-molecular-weight EC materials, for example, there are viologen derivatives that are colored upon reduction (cathodic compounds) and oligothiophene derivatives that are colored upon oxidation (anodic compounds).

In the related art, as applications of EC elements, for example, auto-dimming mirrors of automobiles and electronic paper have been proposed. These EC elements utilize advantages of providing various tones depending on materials selected. This suggests that development of materials of various tones leads to wide-ranging applications. For example, in the case of an application to full-color displays, materials that turn cyan, magenta, or yellow are necessary. In the case of further wide-ranging applications, EC materials that become colored to have various absorption wavelengths are necessary. Thus, organic EC materials, which can be designed to take on various colors by molecular designing, have been attracting attention.

In order to use electrochromic compounds to constitute devices that absorb light of a wide range in the visible-light region, the compounds need to absorb light of various wavelengths. Thus, there has been a demand for various electrochromic compounds.

Patent Literature 1 states that an organic compound represented by a structural formula C-1 below in which a benzene ring is bonded to and disposed between two pyridine rings is colored upon reduction to absorb light at 550 nm. Patent Literature 2 states that an organic compound represented by a structural formula C-2 below is colored upon reduction to absorb light at about 570 nm.

[Chem. 1]

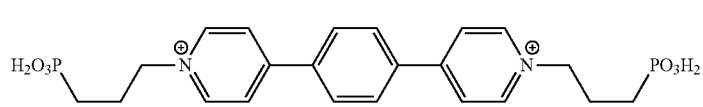

C-1

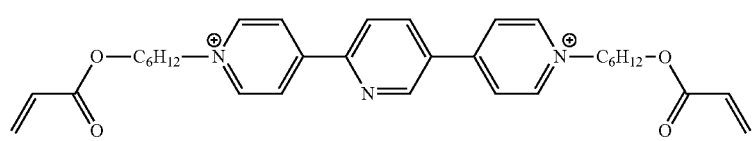

C-2

PTL1 and PTL2 describe, as electrochromic compounds, a compound that becomes colored to absorb light of a wavelength of 550 nm, and a compound that becomes colored to absorb light of a wavelength of 570 nm. One of the methods of changing the absorption wavelength region upon coloration is a method of, in order to change the conjunction structure of the bipyridinium salt skeleton of the chemical structure, increasing or decreasing the number of the ring structures. However, such a simple increase or decrease in the number of the ring structures has not provided electrochromic compounds that have absorption in 450 to 540 nm.

CITATION LIST

Patent Literature

PTL: Japanese Patent Laid-Open No. 2007-171781
PTL2: Japanese Patent Laid-Open No. 2017-203001

SUMMARY OF THE INVENTION

Under such circumstances, the present invention provides a cathodic electrochromic compound that absorbs, upon coloration, light of wavelengths of 450 to 540 nm.

An embodiment of the present invention provides an organic compound represented by the following general formula [1].

[Chem. 2]

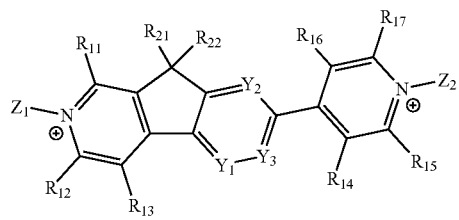

[1]

In the formula, $Z_1$ and $Z_2$ are each independently selected from an alkyl group that may have a substituent, an aryl group that may have a substituent, and an aralkyl group that may have a substituent.

$R_{11}$ to $R_{17}$ are each independently selected from a hydrogen atom and a substituent. The substituent is any one of an alkyl group that may have a substituent, an alkoxy group that may have a substituent, an aryl group that may have a substituent, a heterocyclic group that may have a substituent, and a halogen atom. $R_{21}$ and $R_{22}$ are each independently selected from a hydrogen atom and a substituent. The substituent is any one of an alkyl group that may have a substituent, an aryl group that may have a substituent, and an aralkyl group that may have a substituent.

$Y_1$ to $Y_3$ are each independently selected from a carbon atom, a N atom, and $(N^+\text{-}L)(X^-)$. L is any one of an alkyl group, an aryl group, and an aralkyl group that may have a substituent.

Further features of the present invention will become apparent from the following description of exemplary embodiments with reference to the attached drawings.

DESCRIPTION OF THE EMBODIMENTS

Figure 1:
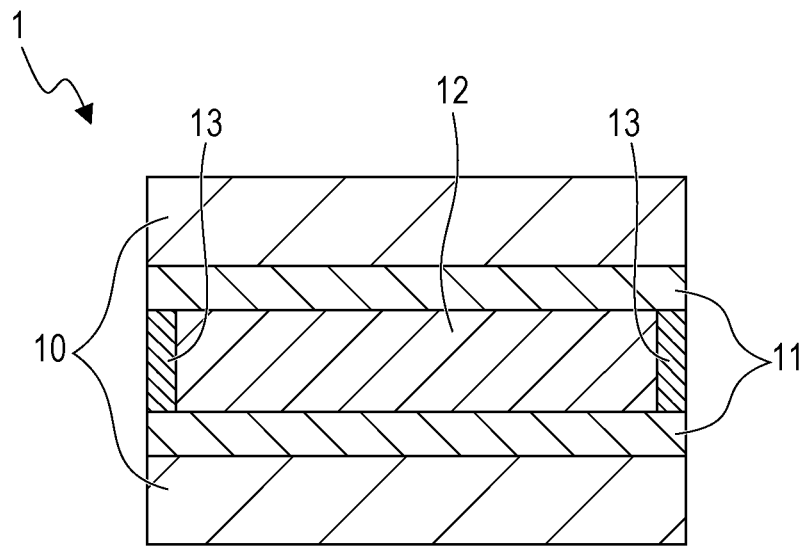
FIG. 1 is a schematic sectional view of an example of an electrochromic element according to an embodiment.

An embodiment of the present invention is an organic compound having electrochromic properties, and is an organic compound represented by a general formula [1].

[Chem. 3]

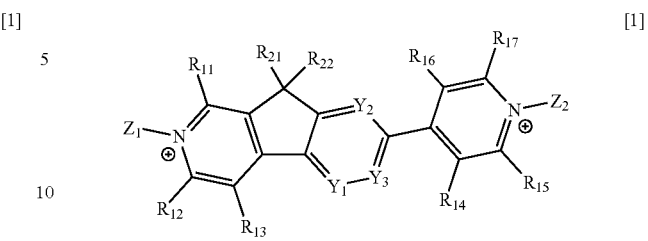

[1]

In the general formula [1], $Z_1$ and $Z_2$ are each independently selected from an alkyl group that may have a substituent, an aryl group that may have a substituent, and an aralkyl group that may have a substituent. $Z_1$ and $Z_2$ are preferably aryl groups that may have a substituent. Such an aryl group may be, for example, a phenyl group or a naphthyl group, and preferably has an alkyl group as a substituent. This alkyl group may be a substituent at the para position with respect to the basic skeleton of the general formula [1]. Alternatively, the alkyl group may be a substituent at an ortho position with respect to the basic skeleton of the general formula [1]. In this case, the alkyl group is preferably an alkyl group having 1 to 8 carbon atoms. In this Description, the basic skeleton used herein means, in the general formula [1], a structure where $Z_1$, $Z_2$, $R_{11}$ to $R_{17}$, $R_{21}$, and $R_{22}$ are all hydrogen atoms.

An organic compound according to an embodiment of the present invention may exist together with a counter ion. When the counter ion is denoted by $X^-$, the organic compound is represented by the following general formula [2].

[Chem. 4]

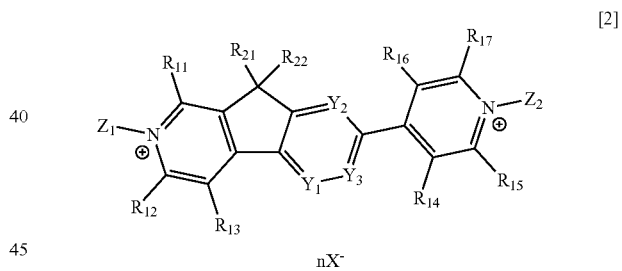

[2]

In the general formula [2], the substituents represented by $Z_1$, $Z_2$, $R_{11}$ to $R_1$, $R_{21}$, and $R_{22}$ are the same as in the general formula [1]. However, $X^-$ represents an anion, and $X^-$'s may be the same or different; n is an integer of 1 or more.

$R_{11}$ to $R_{17}$ are each independently selected from a hydrogen atom and a substituent. The substituent is any one of an alkyl group that may have a substituent, an alkoxy group that may have a substituent, an aryl group that may have a substituent, a heterocyclic group that may have a substituent, and a halogen atom. $R_{16}$ and $R_{17}$ may be linked together to form a ring.

$R_{21}$ and $R_{22}$ are each independently selected from a hydrogen atom and a substituent. This substituent is any one of an alkyl group that may have a substituent, an aryl group that may have a substituent, and an aralkyl group that may have a substituent.

$Y_1$ to $Y_3$ are each independently selected from a carbon atom, a N atom, and $(N^+\text{-}L)(X^-)$. L is any one of an alkyl group, an aryl group, and an aralkyl group that may have a substituent.

$Y_1$ and $Y_2$ may be N atoms or $(N^+-L)(X^-)$, and $Y_3$ may be a carbon atom. Alternatively, $Y_1$ may be a N atom or $(N^+-L)(X^-)$, and the other two may be carbon atoms. Alternatively, $Y_1$ to $Y_3$ may all be carbon atoms.

The alkyl groups represented by $Z_1$, $Z_2$, $R_{11}$ to $R_{17}$, $R_{21}$, and $R_{22}$ preferably have 1 or more and 8 or less carbon atoms, and may be linear, branched, or cyclic. Hydrogen atoms may be replaced by fluorine atoms. Carbon atoms of alkyl groups may be replaced by ester groups or cyano groups.

Specific examples of the alkyl groups include a methyl group, an ethyl group, a normal propyl group, an isopropyl group, a normal butyl group, a tertiary butyl group, an octyl group, a cyclohexyl group, and a trifluoromethyl group.

The alkyl groups represented by $Z_1$ and $Z_2$ may have, at their ends, adsorption groups or acid ester groups thereof for adsorption onto porous electrodes. Specific examples of the adsorption groups or acid ester groups thereof include a carboxyl group and carboxyl ester groups, a sulfonic group and sulfonic ester groups, a phosphonic group and phosphonic ester groups, and trialkoxy silyl groups. Furthermore, in order to improve the solubility in organic solvents, the alkyl groups may have, at their ends, polar groups such as a hydroxyl group and amino groups, and ionic groups such as ammonium, pyridinium, and quinolinium.

Examples of the aryl groups represented by $Z_1$, $Z_2$, $R_{11}$ to $R_{17}$, $R_{21}$, and $R_{22}$ include a phenyl group, a biphenyl group, a tolyl group, a fluorenyl group, a naphthyl group, a fluoranthenyl group, an anthryl group, a phenanthryl group, a pyrenyl group, and perylenyl group. Preferred is a phenyl group.

As the aryl group including a hetero atom (heterocyclic group), examples include a pyridyl group, a thienyl group, an oxazolyl group, an oxadiazolyl group, a thiazolyl group, a thiadiazolyl group, and an indolyl group. Preferred is a pyridyl group.

Such an aryl group may have, as a substituent, a halogen atom, an alkyl group having 1 or more and 6 or less carbon atoms, an alkoxy group having 1 or more and 4 or less carbon atoms, an aryl group, an aralkyl group, a hydroxyl group, a substituted amino group, or a substituted silyl group. Hydrogen atoms of the alkyl group or the alkoxy group may be replaced by halogen atoms, preferably fluorine atoms. When the aryl groups represented by $Z_1$ and $Z_2$ have an alkyl group or alkoxy group, its end may have an adsorption group or its acid ester group for adsorption onto porous electrodes, or may have an ionic group for improvement in the solubility in organic solvents. Specific examples of the adsorption group or its acid ester group and the ionic group are the same as the above-described examples for the alkyl groups represented by $Z_1$ and $Z_2$.

Examples of the aralkyl groups represented by $Z_1$, $Z_2$, $R_{21}$, and $R_{22}$ include a benzyl group and a phenethyl group. The aralkyl groups may have a substituent, and may specifically have an alkyl group having 1 or more and 8 or less carbon atoms, or an alkoxy group having 1 or more and 8 or less carbon atoms. Hydrogen atoms of the alkyl group or the alkoxy group may be replaced by halogen atoms, preferably fluorine atoms.

When the aralkyl groups represented by $Z_1$ and $Z_2$ have an alkyl group or alkoxy group, its end may have an adsorption group or its acid ester group for adsorption onto porous electrodes, or may have an ionic group for improvement in the solubility in organic solvents. Specific examples of the adsorption group or its acid ester group and the ionic group are the same as the above-described examples for the alkyl groups represented by $Z_1$ and $Z_2$.

The alkoxy groups represented by $R_{11}$ to $R_{17}$ may be linear, branched, or cyclic. Such an alkoxy group preferably has 1 or more and 8 or less carbon atoms. Hydrogen atoms of the alkoxy group may be replaced by halogen atoms.

Specific examples include a methoxy group, an ethoxy group, an isopropoxy group, a n-butoxy group, a tert-butoxy group, an ethylhexyloxy group, an octyloxy group, a benzyloxy group, and a trifluoromethoxy group. Of these, particularly preferred are a methoxy group, an ethoxy group, and an isopropoxy group.

Examples of the halogen atoms represented by $R_{11}$ to $R_{17}$ include fluorine, chlorine, bromine, and iodine.

$Y_1$ to $Y_3$ are each independently selected from a carbon atom, a N atom, and $(N^+-L)(X^-)$. L is any one of an alkyl group, an aryl group, and an aralkyl group that may have a substituent. Specific examples of these alkyl group, aryl group, and aralkyl group represented by L are the same as the above-described examples of the alkyl group, aryl group, and aralkyl group represented by $Z_1$ and $Z_2$.

The anion represented by $X^-$ is selected from anions such as $PF_6^-$, $ClO_4^-$, $BF_4^-$, $AsF_6^-$, $SbF_6^-$, $CF_3SO_3^-$, and $(CF_3SO_2)_2N^-$, and halogen anions such as $Br^-$, $Cl^-$, and $I^-$, and is preferably any one of $PF_6^-$, $ClO_4^-$, $BF_4^-$, $CF_3SO_3^-$, and $(CF_3SO_2)_2N^-$. When a plurality of $X^-$'s are included, they may be the same or different.

The method for producing an organic compound according to an embodiment of the present invention is not particularly limited, and it can be produced by, for example, the following method. The compound represented by the general formula [1] above where $Z_1$ and $Z_2$ are an alkyl group and an aralkyl group can be produced by causing a reaction of an organic compound represented by the following general formula [3] and a halide in a predetermined solvent, and subsequently performing an anion exchange reaction with a salt containing a desired anion in a predetermined solvent.

[Chem. 5]

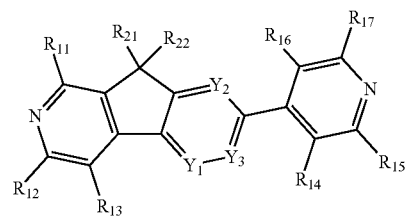

[3]

The compound where $Z_1$ and $Z_2$ are aryl groups can be obtained by causing a reaction between an organic compound represented by the general formula [3] and 2,4-dinitrophenyl halide to form an intermediate where $Z_1$ and $Z_2$ are 2,4-dinitrophenyl groups, causing the intermediate to react with an aryl amine, and performing an anion exchange reaction with a salt containing an anion in a predetermined solvent. By selecting the solvent and the reaction temperature, one of the imines alone may be caused to react. Alternatively, the reaction may be repeated to individually introduce different substituents into the two imines.

The method for producing the above-described general formula [3] is not particularly limited; for example, it can be produced by the following production method as an example.

[Chem. 6]

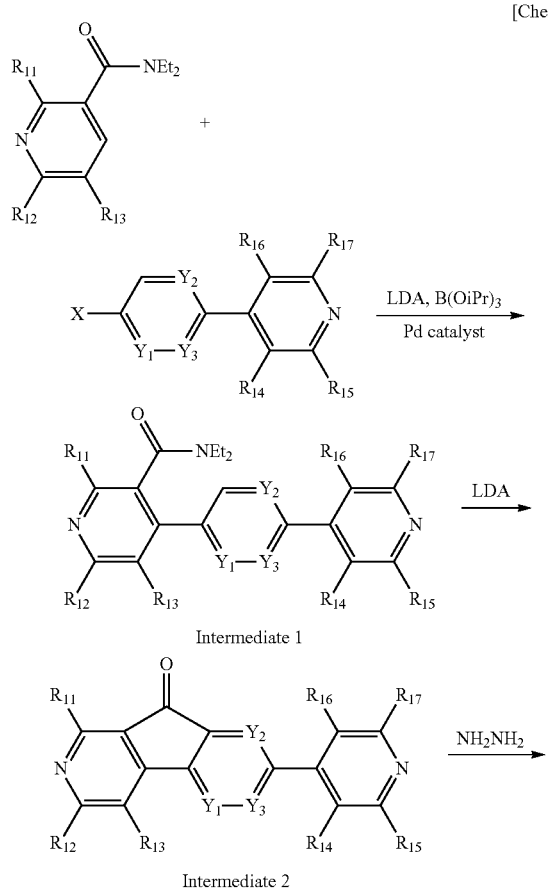

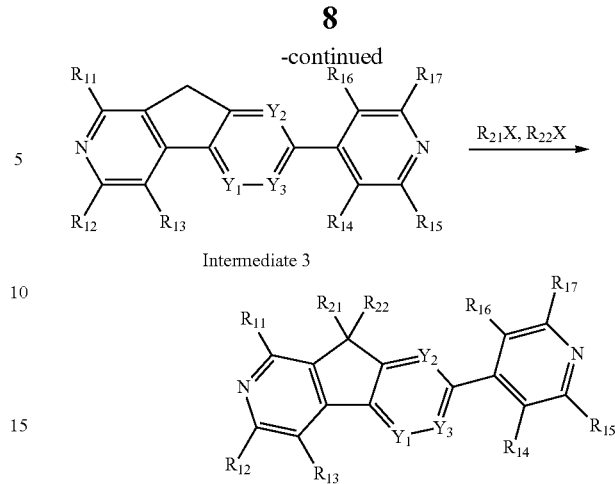

Intermediate 1 can be synthesized by coupling of a N,N-diethylnicotinamide derivative and a 4-halogenopyridylpyridine derivative. Intermediate 1 is treated with LDA (lithium diisopropylamide) to undergo a cyclization reaction to thereby synthesize Intermediate 2. Furthermore, Intermediate 2 is subjected to Wolff-Kishner reduction to thereby synthesize Intermediate 3. The organic compound represented by the general formula [3] can be synthesized by, in the presence of a base, a reaction between Intermediate 3 and a desired halogenated alkyl. Incidentally, as described above, $Y_1$ to $Y_3$ are each independently selected from a carbon atom, a N atom, and $(N^+-L)(X^-)$. In any of these, the synthesis can be achieved by the above-described reaction path.

The following are specific examples of structural formulas of compounds according to the present invention. However, compounds according to the present invention are not limited to these.

[Chem. 7]

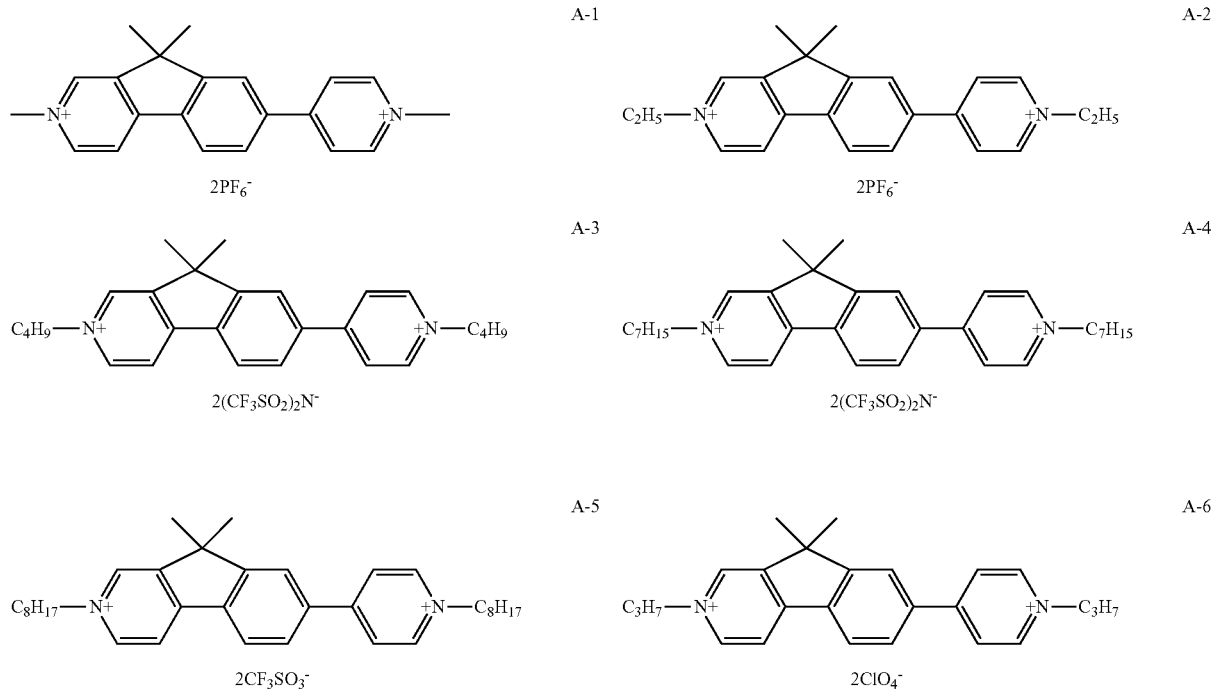

-continued
A-7
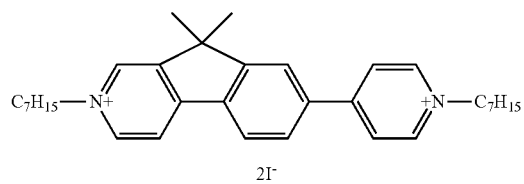
2I⁻
A-8
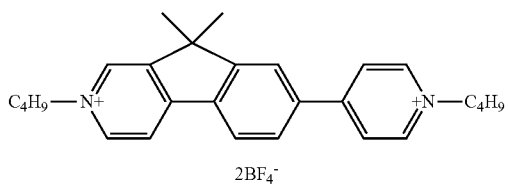
2BF₄⁻
A-9
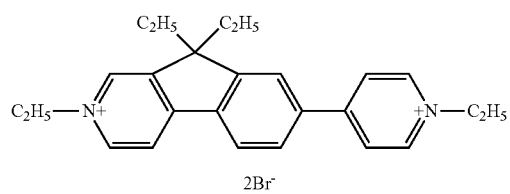
2Br⁻
A-10
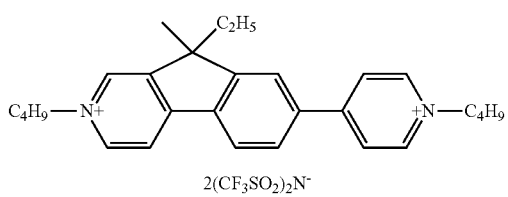
2(CF₃SO₂)₂N⁻
[Chem. 8]
A-11
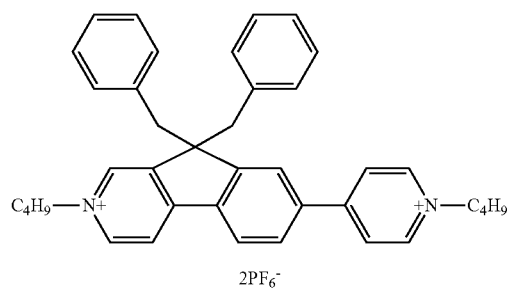
2PF₆⁻
A-12
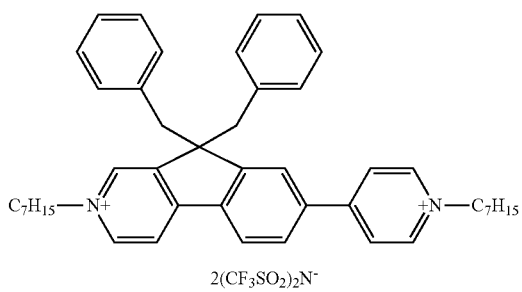
2(CF₃SO₂)₂N⁻
A-13
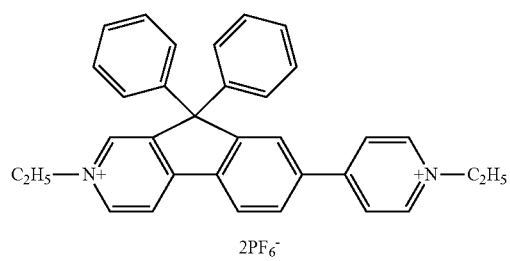
2PF₆⁻
A-14
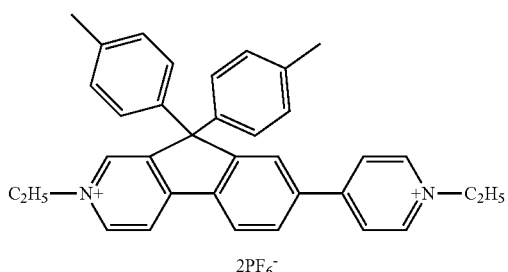
2PF₆⁻
A-15
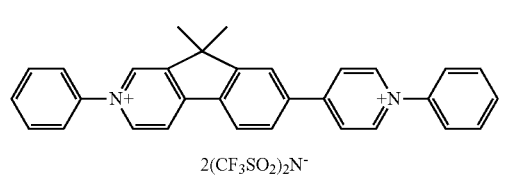
2(CF₃SO₂)₂N⁻
A-16
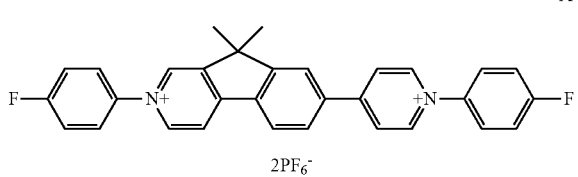
2PF₆⁻
A-17
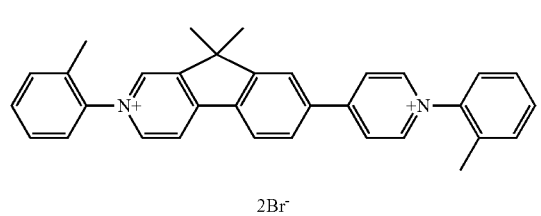
2Br⁻
A-18
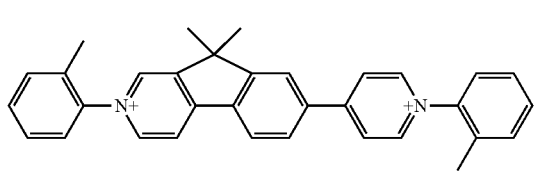
2(CF₃SO₂)₂N⁻
A-19
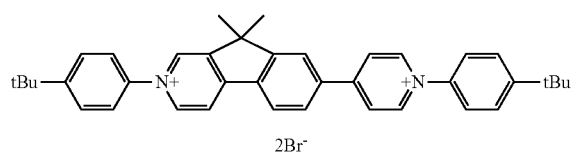
2Br⁻
A-20
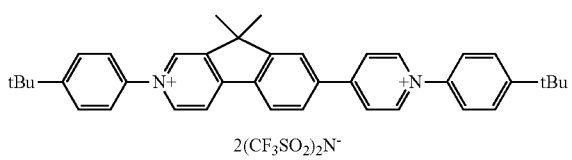
2(CF₃SO₂)₂N⁻

-continued
A-21
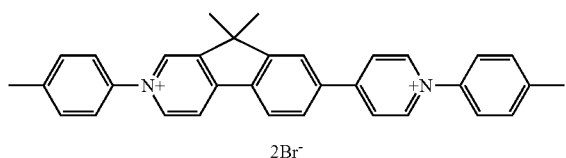
2Br⁻
A-22
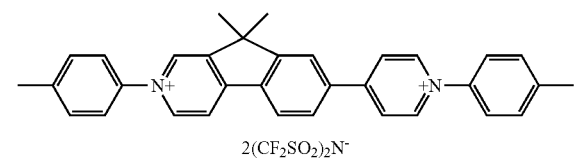
2(CF₂SO₂)₂N⁻
[Chem. 9]
A-23
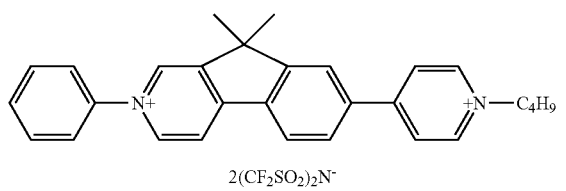
2(CF₂SO₂)₂N⁻
A-24
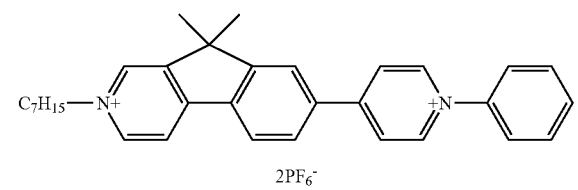
2PF₆⁻
A-25
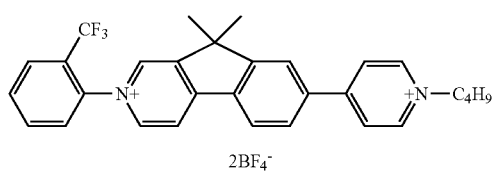
2BF₄⁻
A-26
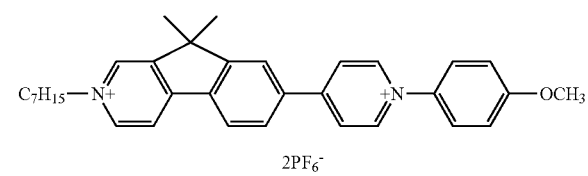
2PF₆⁻
A-27
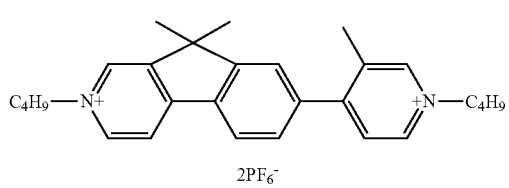
2PF₆⁻
A-28
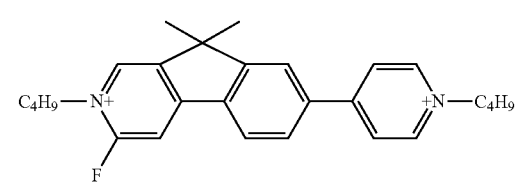
A-28
A-29
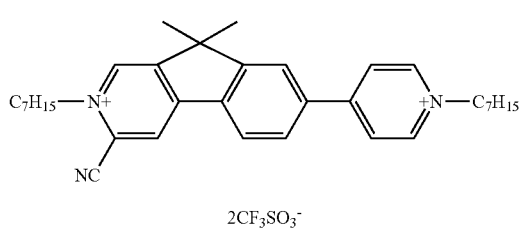
2CF₃SO₃⁻
A-30
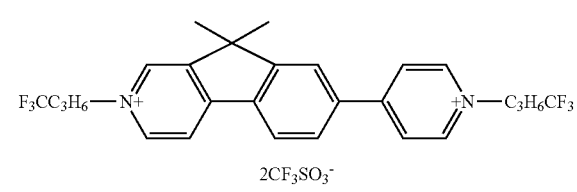
2CF₃SO₃⁻
A-31
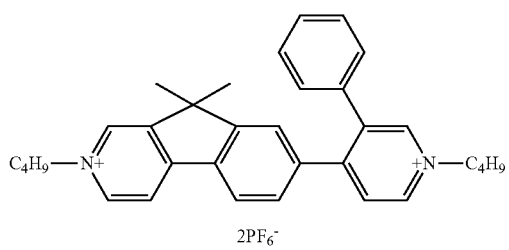
2PF₆⁻
A-32
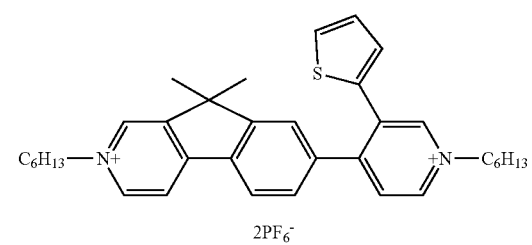
2PF₆⁻
A-33
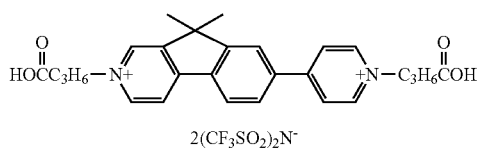
2(CF₃SO₂)₂N⁻
A-34
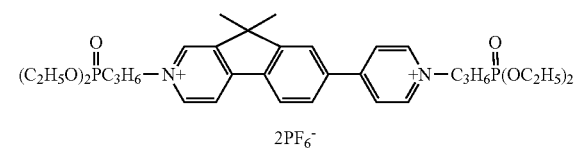
2PF₆⁻

-continued
A-35
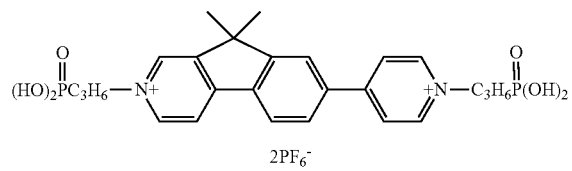
A-36
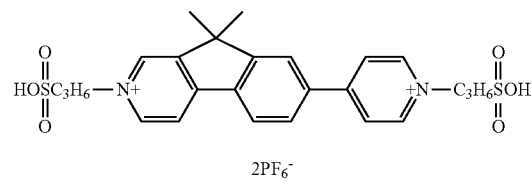
A-37
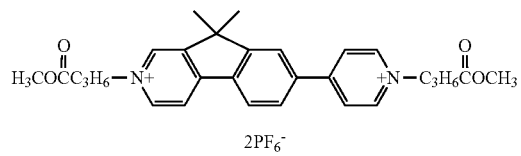
A-38
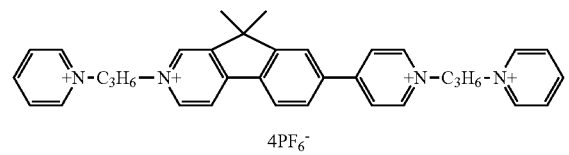
A-39
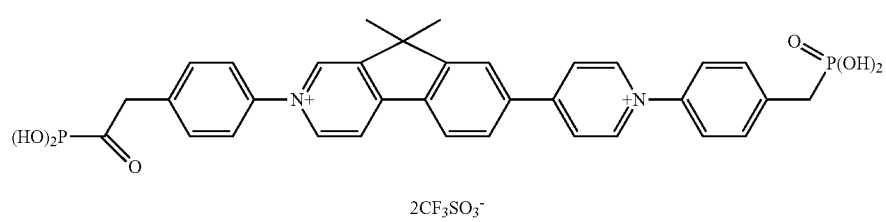
A-40
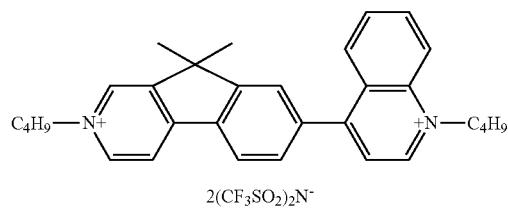
A-41
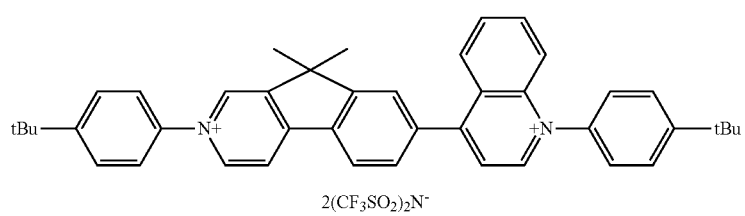
[Chem. 10]
B-1
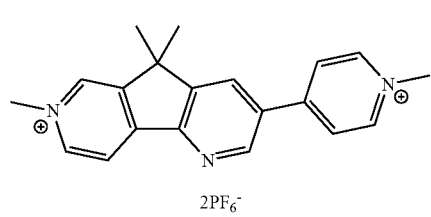
B-2
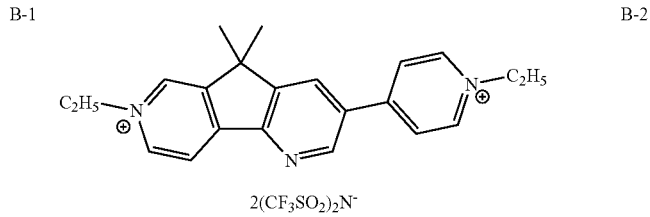
B-3
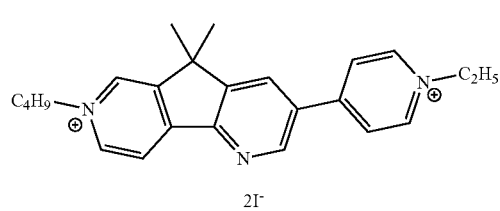
B-4
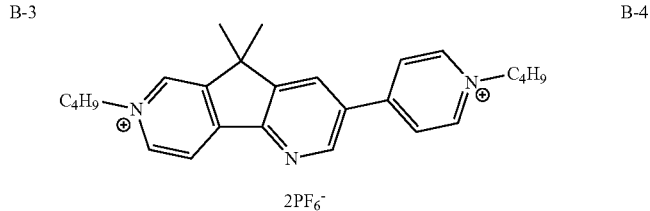

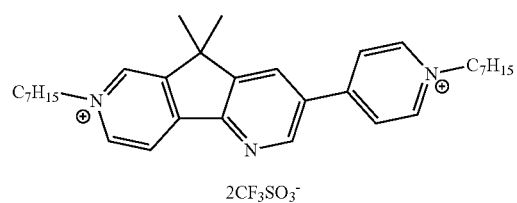
B-5
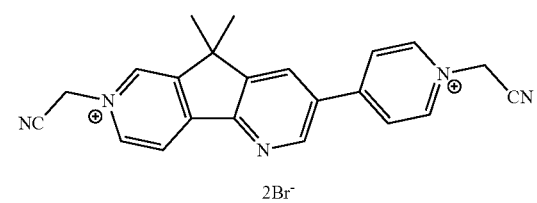
B-6
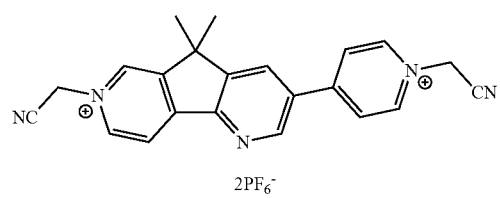
B-7
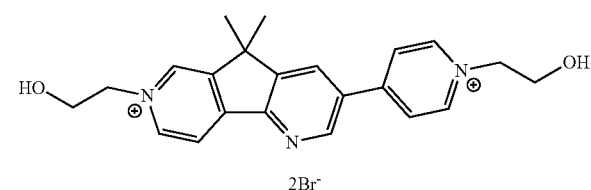
B-8
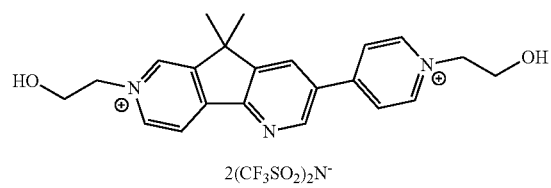
B-9
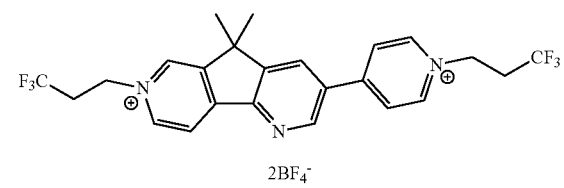
B-10
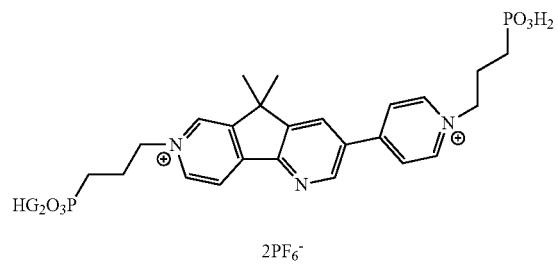
B-11
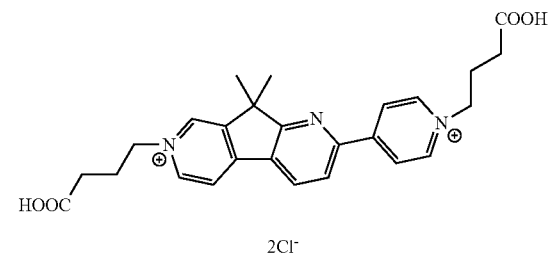
B-12
[Chem. 11]
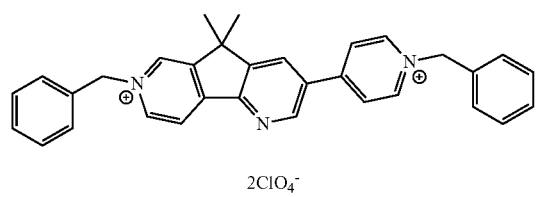
B-13
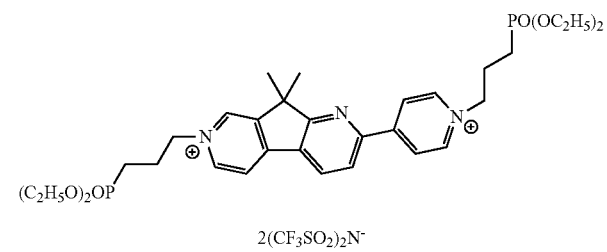
B-14
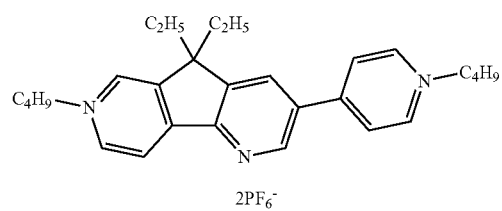
B-15

-continued
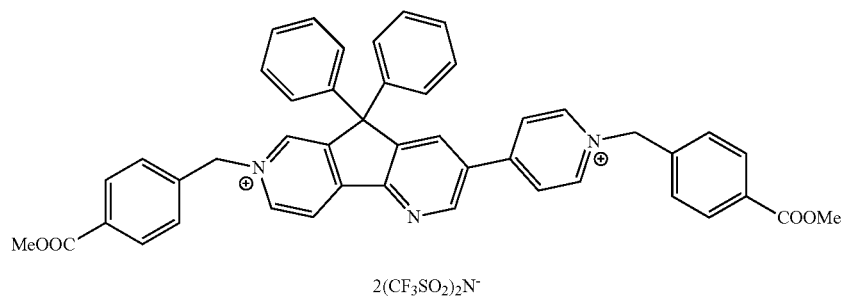
B-16
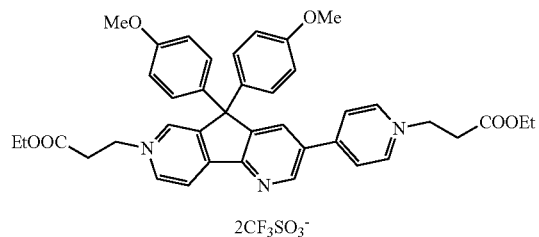
B-17
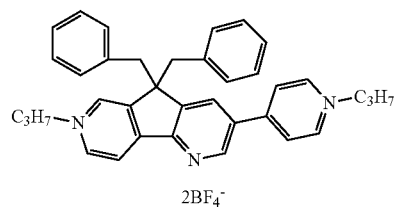
B-18
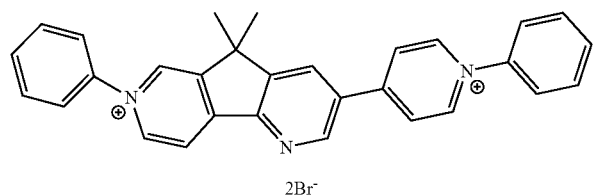
B-19
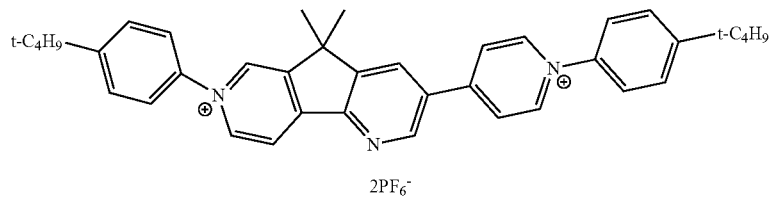
B-20
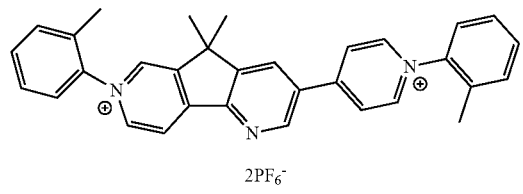
B-21
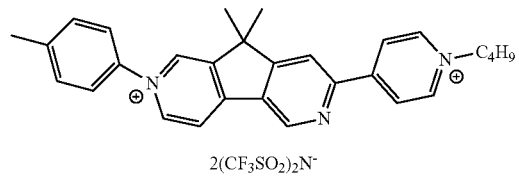
B-22
[Chem. 12]
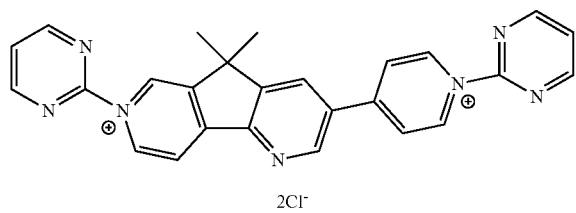
B-23
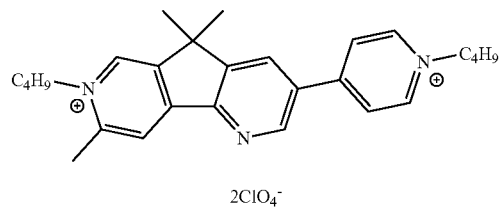
B-24

B-25
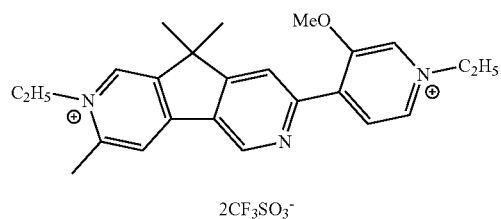
2CF₃SO₃⁻
B-26
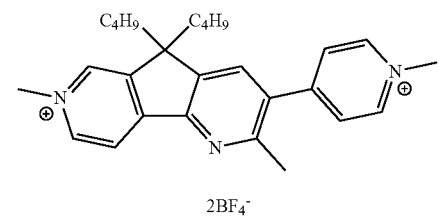
2BF₄⁻
B-27
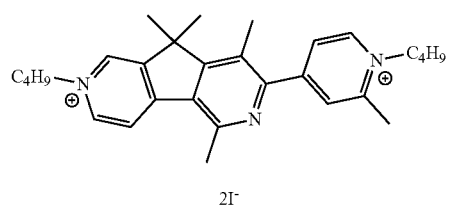
2I⁻
B-28
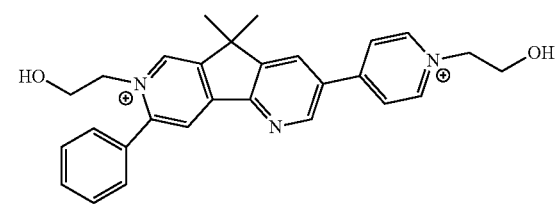
2PF₆⁻
B-29
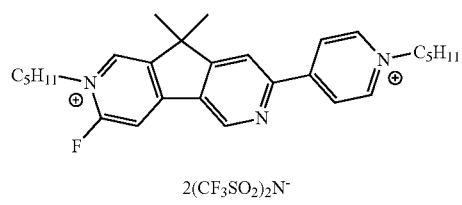
2(CF₃SO₂)₂N⁻
B-30
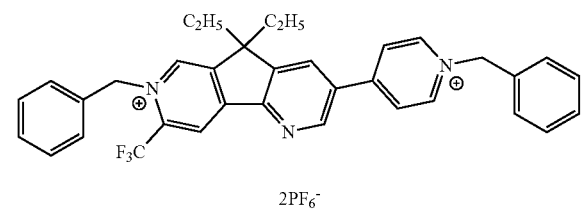
2PF₆⁻
B-31
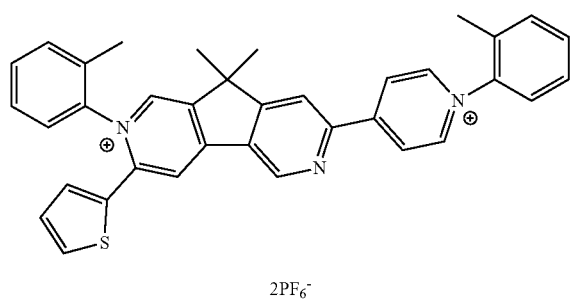
2PF₆⁻
B-32
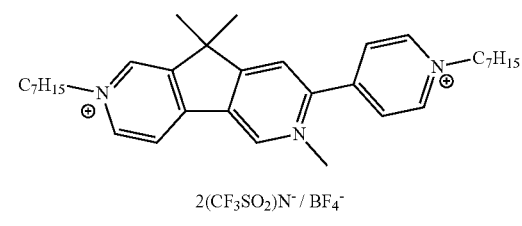
2(CF₃SO₂)N⁻ / BF₄⁻
[Chem. 13]
B-33
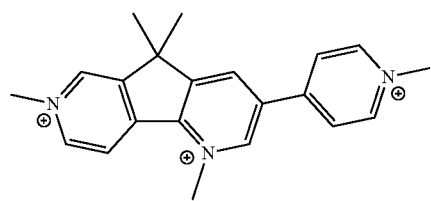
2PF₆⁻ / BF₄⁻
B-34
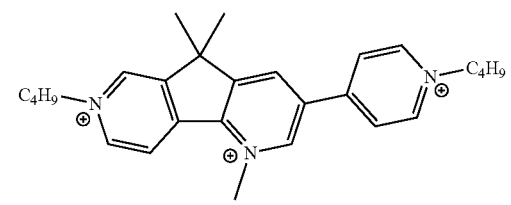
2PF₆⁻ / BF₄⁻
B-35
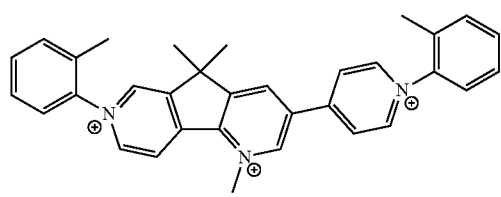
2(CF₃SO₂)₂N⁻ / BF₄⁻
B-36
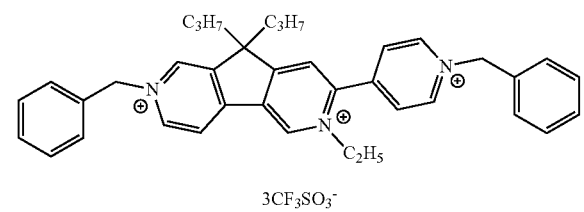
3CF₃SO₃⁻

-continued
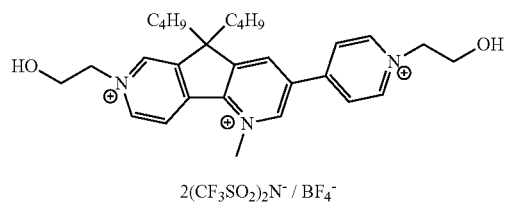
B-37
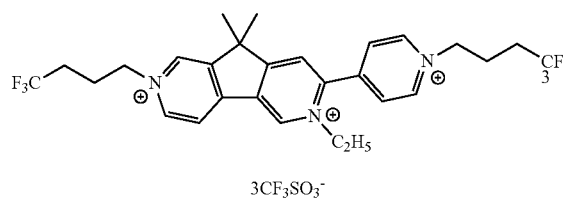
B-38
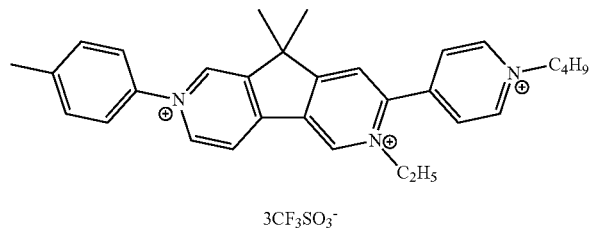
B-39
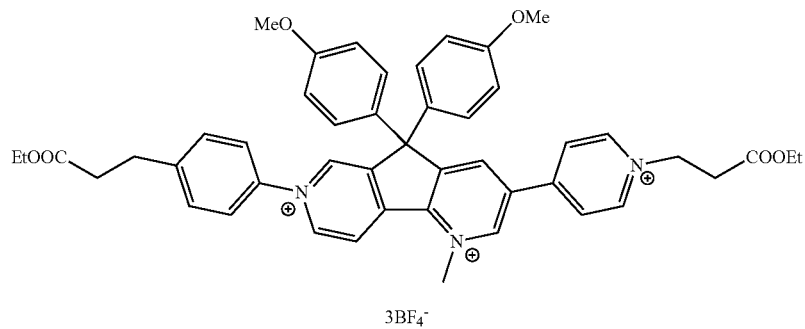
B-40
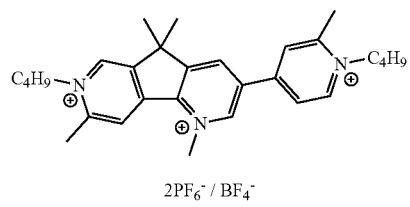
B-41
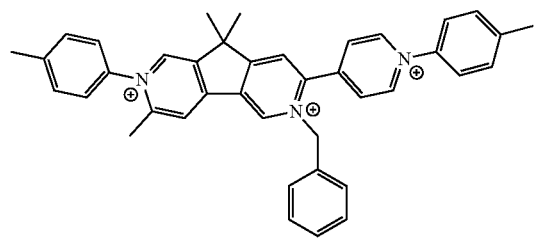
B-42
[Chem. 14]
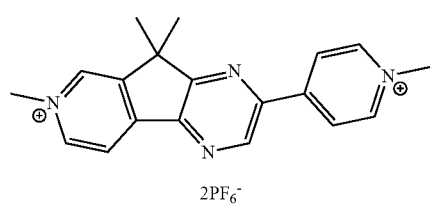
C-1
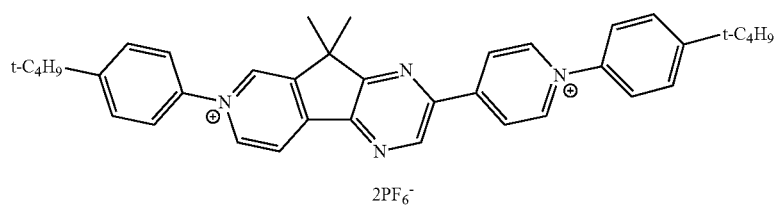
C-2

-continued

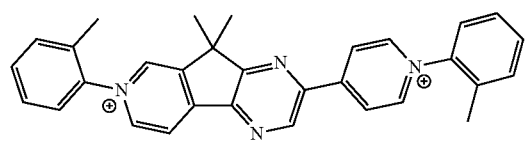
C-3
2BF$_4^-$

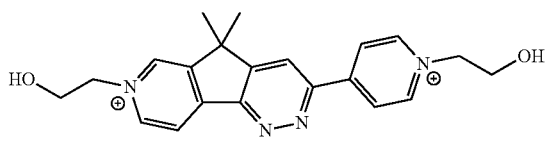
C-4
2(CF$_3$SO$_2$)$_2$N$^-$

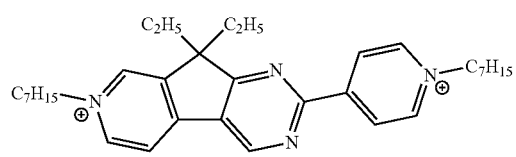
C-5
2CF$_3$SO$_3^-$

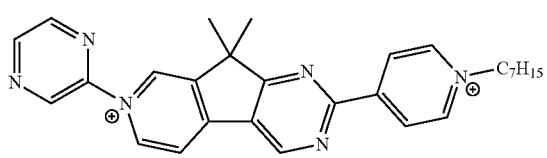
C-6
2(CF$_3$SO$_2$)$_2$N$^-$

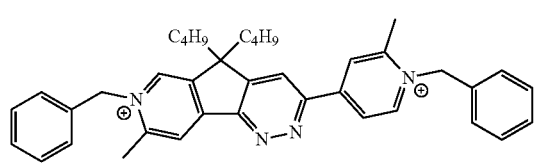
C-7
2ClO$_4^-$

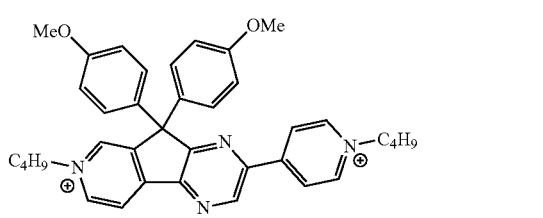
C-8
2(CF$_3$SO$_2$)$_2$N$^-$

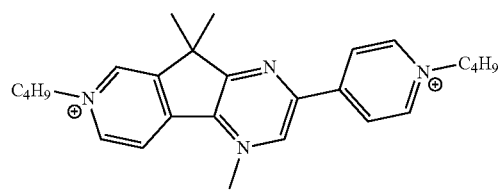
C-9
2PF$_6^-$ / BF$_4^-$

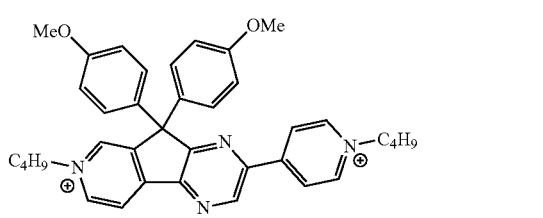
C-10
3(CF$_3$SO$_2$)$_2$N$^-$

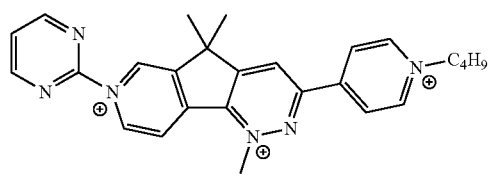
C-11
3BF$_4^-$

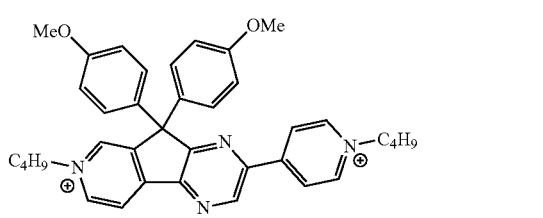
C-12
2PF$_6^-$ / BF$_4^-$

Of the Example compounds, the compounds in the group A are compounds where $Y_1$ to $Y_3$ in the general formula [1] are all carbon atoms.

Of the Example compounds, the compounds in the group B are compounds having a structure where one of $Y_1$ to $Y_3$ in the general formula [1] is a N atom or (N$^+$-L)(X$^-$), and the other two are carbon atoms.

On the other hand, the compounds in the group C are examples of a compound having a chemical structure where two of $Y_1$ to $Y_3$ in the general formula [1] are N atoms or (N$^+$-L)(X$^-$), and the other one is a carbon atom.

Hereinafter, properties based on the structure of an organic compound according to an embodiment of the present invention will be described. The organic compound represented by the general formula [1] is a cathodic EC compound that is colored in the reduction state. Specifically, the organic compound represented by the general formula [1] is a compound in which an electrochemical oxidation-reduction reaction reversibly proceeds, so that its optical absorption properties (the coloration state and light transmittance) change.

An organic compound according to an embodiment of the present invention has the structure represented by the general formula [1], so that it absorbs, upon coloration, light of wavelengths of 450 to 540 nm.

One of desirable properties of electrochromic elements is low-voltage driving. This is because low-voltage driving achieves a reduction in the power consumption, to thereby provide driving for long hours and improved cycling durability. In order to provide low-voltage driving, the compound preferably has a LUMO (lowest unoccupied molecular orbital) level that is low. The "LUMO level is low" is, stated another way, the LUMO level is deep or farther from the vacuum level, or the absolute value of LUMO is large.

Ina cathodic EC compound represented by the general formula [1] according to an embodiment of the present invention, the central aromatic ring linking together two pyridine rings is a heterocycle including a N atom. Thus, the electron density is low, and LUMO is stabilized (deep), to thereby facilitate entry of electrons, stated another way, to cause a shift of the reduction potential in the positive direction.

As examples for performing comparison in terms of the correlation between this chemical structure and the reduction potential, organic compounds (B-4, B-20, and B-21) and (C-1, C-2, and C-3) according to an embodiment of the present invention and Reference compounds (Ref-1, Ref-2, and Ref-3) were examined by molecular orbital calculations.

[Chem. 15]

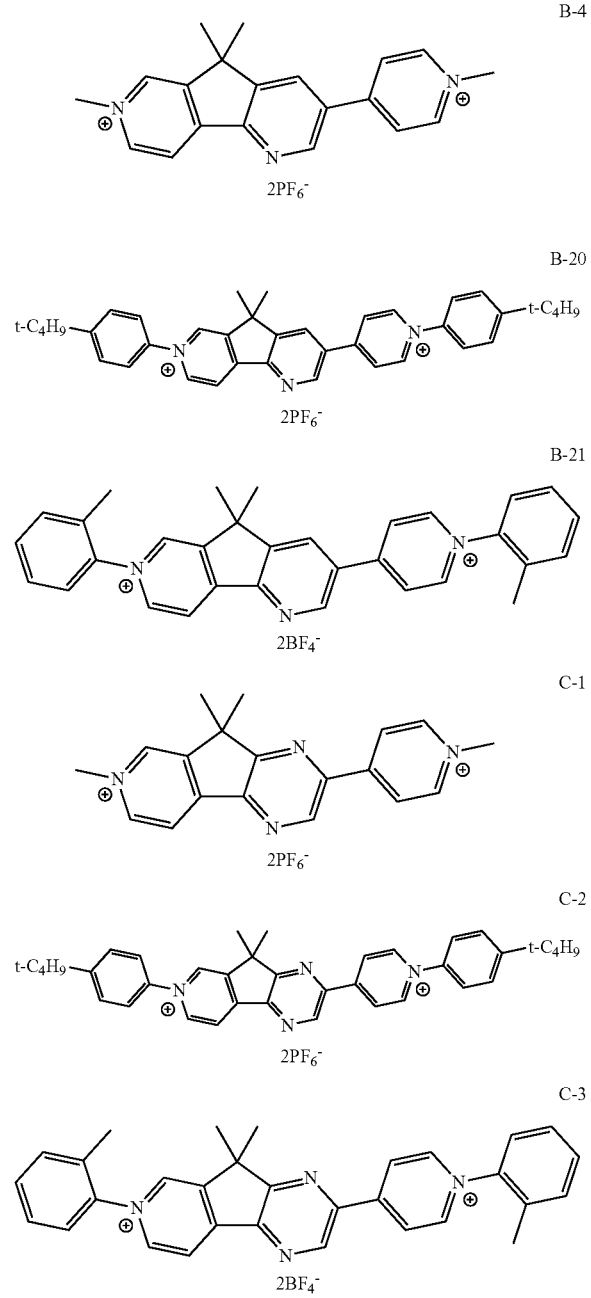

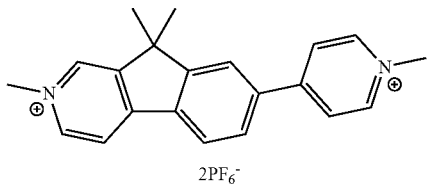

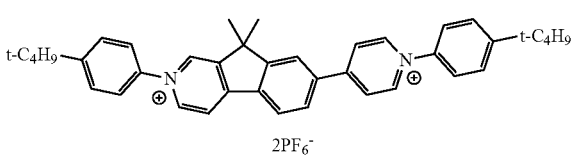

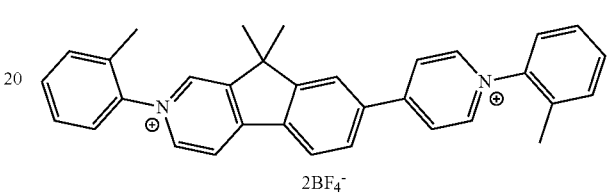

Incidentally, the compounds (B-4, B-20, and B-21) have the central aromatic ring having a single N atom, namely, a pyridine ring; the compounds (C-1, C-2, and C-3) have the central aromatic ring having two N atoms, namely a pyrazine ring. The comparative compounds (Ref-1, Ref-2, and Ref-3) have the central aromatic ring not having N atoms, namely a benzene ring, but the other chemical structures are the same as those of the organic compounds (B-4, B-20, and B-21) and (C-1, C-2, and C-3) according to an embodiment of the present invention. The reduction potentials determined by molecular orbital calculations are summarized in the following Table 1 to Table 3.

TABLE 1

| Compound No. | Reduction potential |
| --- | --- |
| B-4 | −1.18 V |
| C-1 | −0.93 V |
| Ref-1 | −1.28 V |

TABLE 2

| Compound No. | Reduction potential |
| --- | --- |
| B-20 | −1.09 V |
| C-2 | −0.85 V |
| Ref-2 | −1.17 V |

TABLE 3

| Compound No. | Reduction potential |
| --- | --- |
| B-21 | −1.10 V |
| C-3 | −0.85 V |
| Ref-3 | −1.19 V |

As described in Table 1 to Table 3, it has been confirmed that the compounds (B-4, B-20, and B-21) and (C-1, C-2, and C-3) according to an embodiment of the present invention have reduction potentials sifting in the positive direction, compared with the reduction potentials of Reference compounds (Ref-1, Ref-2, and Ref-3). Compared with the Reference compounds, the organic compounds according to an embodiment of the present invention contribute to the low-voltage driving of EC elements.

Incidentally, the molecular orbital calculations were performed by geometry optimization calculations in the ground state using an electron state calculation software, Gaussian 03*Revision D.01. At this time, as the quantum chemistry calculation method, Density Functional Theory was employed. As the functional, B3LYP was employed. As the basis function, in Gaussian 03, Revision D.01, 6-31G* was employed.

The program used for performing these calculations was Gaussian 09, Revision D.01 (M. J. Frisch, G. W. Trucks, H. B. Schlegel, G. E. Scuseria, M. A. Robb, J. R. Cheeseman, G. SCALMANI, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2013.).

An organic compound according to an embodiment of the present invention can be used for the EC layer of an electrochromic element.

Hereinafter, an EC element according to this embodiment will be described with reference to drawings.

In FIG. 1, the EC element includes a pair of transparent electrodes 11, and an EC layer 12 disposed between the pair of electrodes and including an electrolyte and an EC organic compound according to the present invention. The pair of electrodes are disposed so as to have a constant distance between the electrodes using a sealing material 13. In this EC element, the pair of electrodes are disposed between a pair of transparent substrates 10.

The EC layer 12 contains an organic compound according to the present invention. This EC layer may include a layer composed of the EC compound and a layer composed of the electrolyte. Alternatively, the EC layer may be provided as a solution containing the EC compound and the electrolyte. The EC element according to this embodiment is preferably an EC element in which the EC layer is a solution layer.

Hereinafter, members constituting the EC element according to this embodiment will be described.

The electrolyte is not limited as long as it is an ion-dissociable salt that has high solubility in a solvent, or has, in the case of a solid electrolyte, high compatibility with a solvent. In particular, electron-donating electrolytes are preferred. Such electrolytes may also be referred to as supporting electrolytes.

Examples of the electrolyte include inorganic ion salts such as various alkali metal salts and alkaline-earth metal salts, quaternary ammonium salts, and cyclic quaternary ammonium salts.

Specific examples include salts of alkali metals of Li, Na, and K such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, and $KCl$; and quaternary ammonium salts and cyclic quaternary ammonium salts such as $(CH_3)_4NBF_4$, $(C_2H)_4NBF_4$, $(n-C_4H_9)_4NBF_4$, $(n-C_4H_9)_4NPF_6$, $(C_2H_5)_4NBr$, $(C_2H_5)_4NClO_4$, and $(n-C_4H_9)_4NClO_4$.

The solvent in which the EC organic compound and the electrolyte are dissolved is not particularly limited as long as the EC organic compound and the electrolyte are dissolved therein; in particular, polar solvents are preferred.

Specific examples include water and organic polar solvents such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionitrile, 3-methoxypropionitrile, benzonitrile, dimethylacetamide, methylpyrrolidinone, and dioxolane. These may be used alone or in combination of two or more thereof.

Such an EC medium may be made to further contain a polymer or a gelling agent to thereby be turned into a highly viscous medium or a gel medium, for example. Such a polymer or gelling agent may also be referred to as a thickener. The EC solution can be made to contain a thickener to have an increased viscosity, so that the organic compound becomes less likely to form aggregate, to reduce the temperature dependency of the absorption spectrum. Thus, the EC solution preferably contains the thickener.

The EC solution may have a viscosity of 10 to 5000 cP, or 50 to 1000 cP. The EC solution may have a viscosity of 150 cP or less, preferably 100 cP or less, more preferably 65 cP or less. The EC solution may have a viscosity of 20 cP or more, preferably 50 cP or more.

The thickener may have a weight ratio of 20 wt % or less relative to 100 wt % of the weight of the electrochromic layer, preferably 1 wt % or more and 15 wt % or less, more preferably 5 wt % or more and 10 wt % or less.

The polymer is not particularly limited, and examples include polyacrylonitrile, carboxymethylcellulose, polyvinyl chloride, polyethylene oxide, polypropylene oxide, polyurethane, polyacrylate, polymethacrylate, polyamide, polyacrylamide, polyester, and NAFION (registered trademark).

Hereinafter, the transparent substrates and the transparent electrodes will be described. The transparent substrates 10 may be formed of, for example, colorless or color glass, tempered glass, or colorless or color transparent resin. Incidentally, in this embodiment, "transparent" means that the visible-light transmittance is 70% or more.

Specific examples include polyethylene terephthalate, polyethylene naphthalate, polynorbornene, polyamide, polysulfone, polyether sulfone, polyether ether ketone, polyphenylene sulfide, polycarbonate, polyimide, and polymethyl methacrylate.

Examples of the electrode materials for electrodes 11 include metals and metal oxides such as indium tin oxide alloy (ITO), fluorine-doped tin oxide (FTO), tin oxide (NESA), indium zinc oxide (IZO), silver oxide, vanadium oxide, molybdenum oxide, gold, silver, platinum, copper, indium, and chromium, silicon-based materials such as polycrystalline silicon and amorphous silicon, and carbonaceous materials such as carbon black, graphite, and glassy carbon.

Other preferred examples include conductive polymers having conductivities increased by, for example, doping treatment, such as complexes between polystyrene sulfonate and polyaniline, polypyrrole, polythiophene, polyacetylene, polyparaphenylene, or polyethylene dioxythiophene (PEDOT).

In order to hold the EC layer between the pair of electrodes, or in order to keep the distance between the two electrodes, the sealing material 13 is preferably used. The sealing material 13 may contain, for example, a spacer material to thereby have a function of keeping the distance between the electrodes. The sealing material 13 is disposed between the pair of electrodes 11, to provide a space for containing the solution containing an EC organic compound according to the present invention. This sealing material 13 is preferably a material that is chemically stable, is less permeable to gas and liquid, and does not inhibit the oxidation-reduction reaction of the EC compound. Specific examples include inorganic materials such as glass frit, thermosetting or photocurable materials such as epoxy or acrylic resins, polyimide, polytetrafluoroethylene, and fluororubber.

The EC element according to this embodiment may have a liquid injection port provided by the pair of electrodes and the spacer. A composition containing the EC organic compound is injected through the liquid injection port, then the injection port is covered with a sealing member, and further sealed with an adhesive, for example, to thereby provide the element. The sealing member also has a role of preventing contact between and providing isolation between the adhesive and the EC organic compound.

The method for forming the EC element according to this embodiment is not particularly limited, and the following method can be employed: a liquid prepared in advance so as to contain the EC organic compound is injected into a space between the pair of electrodes by, for example, a vacuum injection process, an air injection process, or a meniscus process. The pair of electrodes may each be an electrode substrate in which an electrode and a substrate are integrated.

The EC element 1 according to this embodiment may contain an organic compound according to the present invention and a second organic compound different from this organic compound. The second organic compound may be of a single species or a plurality of species, and may be an anodic EC compound that becomes colored in the oxidation state, a cathodic EC compound that becomes colored in the reduction state, or a compound having both of these properties. Since an organic compound according to the present invention is a compound that becomes colored in the reduction state, the second organic compound is preferably an anodic EC compound that becomes colored in the oxidation state.

The electrochromic layer may have a structure containing four or more species of electrochromic compounds, to thereby provide a flatter absorption spectrum.

The anodic EC compound that becomes colored in the oxidation state is a compound that has, in the oxidation state, a visible-light transmittance lower than the visible-light transmittance in the reduction state. This change in the transmittance occurs at least partially in the visible-light region, and is not required to occur over the entire visible-light region.

In addition to the second organic compound, a third organic compound may be contained. In the case of containing the third organic compound having, in the colored state, an absorption wavelength region different from that of an organic compound according to the present invention or the second organic compound, the EC element can be controlled to absorb light in a wide range. This third organic compound may be an anodic EC compound or a cathodic EC compound.

Such another EC compound preferably has, in the decolored state, an absorption wavelength region of 400 nm or less in the decolored state. This is because an element having high transparency in the decolored state can be provided. On the other hand, the absorption wavelength region in the colored state is preferably 400 nm or more and 800 nm or less, more preferably 400 nm or more and 450 nm or less, or 600 nm or more and 700 nm or less.

Such another EC compound is preferably contained, to thereby provide an EC element that uniformly absorbs light of individual wavelengths in the visible-light region.

Examples of another EC compound in this embodiment include compounds having the following structural formulas.

Examples of another EC compound that becomes colored in the oxidation state include oligothiophenes; phenazine-based compounds such as 5,10-dihydro-5,10-dimethylphenazine, and 5,10-dihydro-5,10-diisopropylphenazine; metallocene-based compounds such as ferrocene, tetra-t-butylferrocene, and titanocene; phenylenediamine-based compounds such as N,N',N,N'-tetramethyl-p-phenylenediamine; and pyrazoline-based compounds such as 1-phenyl-2-pyrazoline.

Examples of the compound that becomes colored in the reduction state include viologen-based compounds such as N,N'-diheptylbipyridinium diperchlorate, N,N'-diheptylbipyridinium bis(tetrafluoroborate), N,N'-diheptylbipyridinium bis(hexafluorophosphate), N,N'-diethylbipyridinium diperchlorate, N,N'-diethylbipyridinium bis(tetrafluoroborate), N,N'-diethylbipyridinium bis(hexafluorophosphate), N,N'-dibenzylbipyridinium diperchlorate, N,N'-dibenzylbipyridinium bis(tetrafluoroborate), N,N'-dibenzylbipyridinium bis(hexafluorophosphate), N,N'-diphenylbipyridinium diperchlorate, N,N'-diphenylbipyridinium bis(tetrafluoroborate), and N,N'-diphenylbipyridinium bis(hexafluorophosphate); anthraquinone-based compounds such as 2-ethylanthraquinone, 2-t-butylanthraquinone, and octamethylanthraquinone; ferrocenium salt-based compounds such as ferrocenium tetrafluoroborate, and ferrocenium hexafluorophosphate; and styryl-based compounds.

In this embodiment, the phenazine-based compounds are compounds having, in the chemical structure, a 5,10-dihydro-phenazine skeleton. The phenazine-based compounds encompass substituted 5,10-dihydrophenazine compounds. For example, hydrogen atoms at 5 and 10 positions of 5,10-dihydrophenazine may be substituted with alkyl groups such as a methyl group, an ethyl group, and a propyl group, or aryl groups such as a phenyl group. The phenazine-based compounds may be 5,10-dihydrophenazine compounds having an alkyl group having 1 or more and 20 or less carbon atoms, 5,10-dihydrophenazine compounds having an alkoxy group having 1 or more and 20 or less carbon atoms, or 5,10-dihydrophenazine compounds having an aryl group having 4 or more and 60 or less carbon atoms. The same applies to other compounds such as the viologen-based compounds.

The compounds contained in the EC layer 12 of the EC element 1 according to this embodiment can be extracted and analyzed by publicly known methods, to thereby confirm their presence in the EC element 1. For example, the compounds may be extracted by chromatography, and analyzed by NMR. Alternatively, when the electrochromic layer is solid, the compounds may be analyzed by, for example, TOF-SIMS.

The EC element according to this embodiment has high transparency in the decolored state, but, in the colored state, provides high optical density to lower the transmittance, and hence is suitably used for considerably reducing the amount of light incident on image pickup apparatuses such as cameras.

The EC element 1 according to this embodiment is applicable to, for example, optical filters, lens units, image pickup apparatuses, and window members. Alternatively, the EC element according to this embodiment, and a light reflection member including the EC element on the light reflection surface may constitute an electrochromic mirror. The light reflection member may also function as an electrode or a substrate.

An optical filter according to an embodiment of the present invention includes the EC element 1 and an active element connected to the EC element 1. The active element drives the electrochromic element, to regulate the amount of light passing through the electrochromic element. The active element is, for example, a transistor or a MIM element. The transistor may contain, in the active region, an oxide semiconductor such as InGaZnO.

Figure 2:
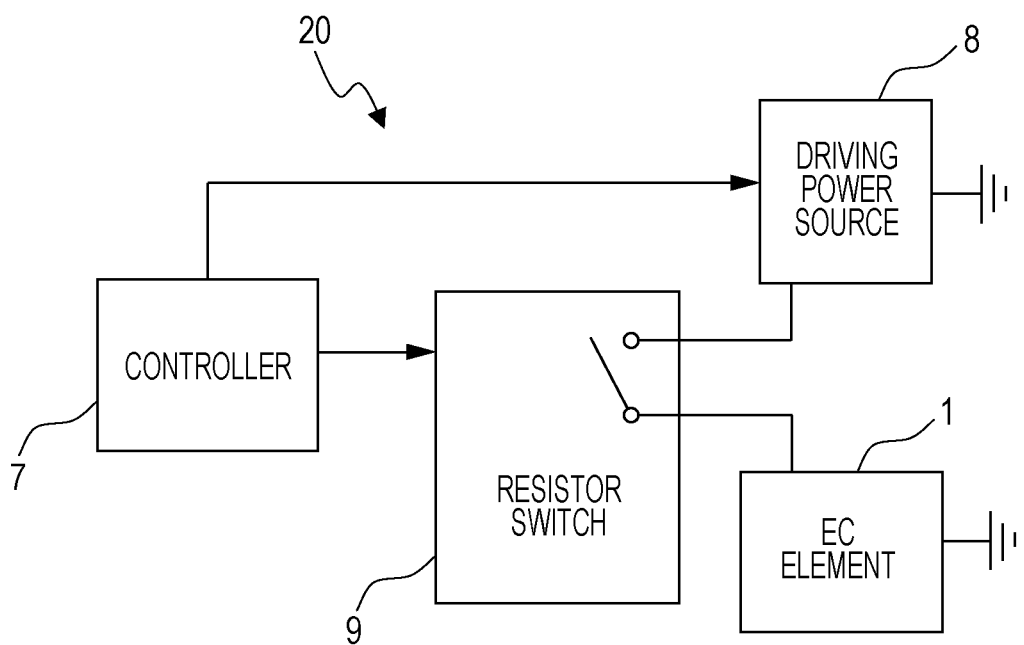
FIG. 2 is a schematic view illustrating an example of a driving device connected to an electrochromic element according to an embodiment.

The optical filter includes the EC element 1 according to this embodiment and a driving device connected to the EC element 1. FIG. 2 is a schematic view illustrating an example of a driving device 20 for the EC element 1, and the EC element 1 driven by the driving device 20. The driving device 20 for the EC element 1 according to this embodiment includes a driving power source 8, a resistor switch 9, and a controller 7.

The driving power source 8 applies, to the EC element 1, a voltage for causing the electrochemical reaction of the EC material in the EC layer 12.

As the method of using the controller 7 to control the transmittance of the EC element, a method suitable for the element is employed. Specific examples are as follows: a method of inputting, to the EC element 1, predetermined conditions for a desired transmittance set value, and a method of comparing the transmittance set value and the transmittance of the EC element 1, and inputting conditions selected so as to satisfy the set value. Examples of the parameters changed include voltage, current, and a duty ratio. To the EC element 1, the controller 7 increases or decreases voltage in the voltage control mode, current in the current control mode, or a duty ratio in the pulse-duration modulation mode, to increase or decrease the color concentration of the corresponding EC element, to thereby decrease or increase the amount of incident light.

The resistor switch 9 enables, in the closed circuit including the driving power source 8 and the EC element 1, switching between resistor $R_1$ (not shown) and resistor $R_2$ (not shown) having a higher resistance than the resistor $R_1$ to provide a series connection. The resistor $R_1$ preferably has a resistance at least lower than the highest impedance of the element closed circuit, preferably 10Ω or less. The resistor $R_2$ preferably has a resistance higher than the highest impedance of the element closed circuit, preferably 1 Mf or higher. Incidentally, the resistor $R_2$ may be the air. In this case, strictly, the closed circuit is an open circuit; however, the air can be regarded as the resistor $R_2$, which provides a closed circuit. The controller 7 transmits switching signals to the resistor switch 9, to control switching between the resistor $R_1$ and the resistor $R_2$.

The lens unit according to this embodiment includes a plurality of lenses, and an optical filter including the EC element 1. The optical filter may be disposed between the plurality of lenses or outside of the lenses. The optical filter is preferably disposed on the optical axis of the lenses.

The image pickup apparatus according to this embodiment includes an optical filter, and a light-receiving element that receives light having passed through the optical filter.

Specific examples of the image pickup apparatus include cameras, video cameras, and camera-equipped cellular phones. The image pickup apparatus may have a structure in which a body including a light-receiving element, and a lens unit including a lens are separable from each other.

In such a case where the body and the lens unit of the image pickup apparatus are separable from each other, images may be captured using an optical filter separable from the image pickup apparatus, which also falls within the scope of the present invention. Incidentally, in this case, the optical filter may be disposed, for example, outside of the lens unit, between the lens unit and the light-receiving element, or between a plurality of lenses (when the lens unit includes a plurality of lenses).

Figure 3A:
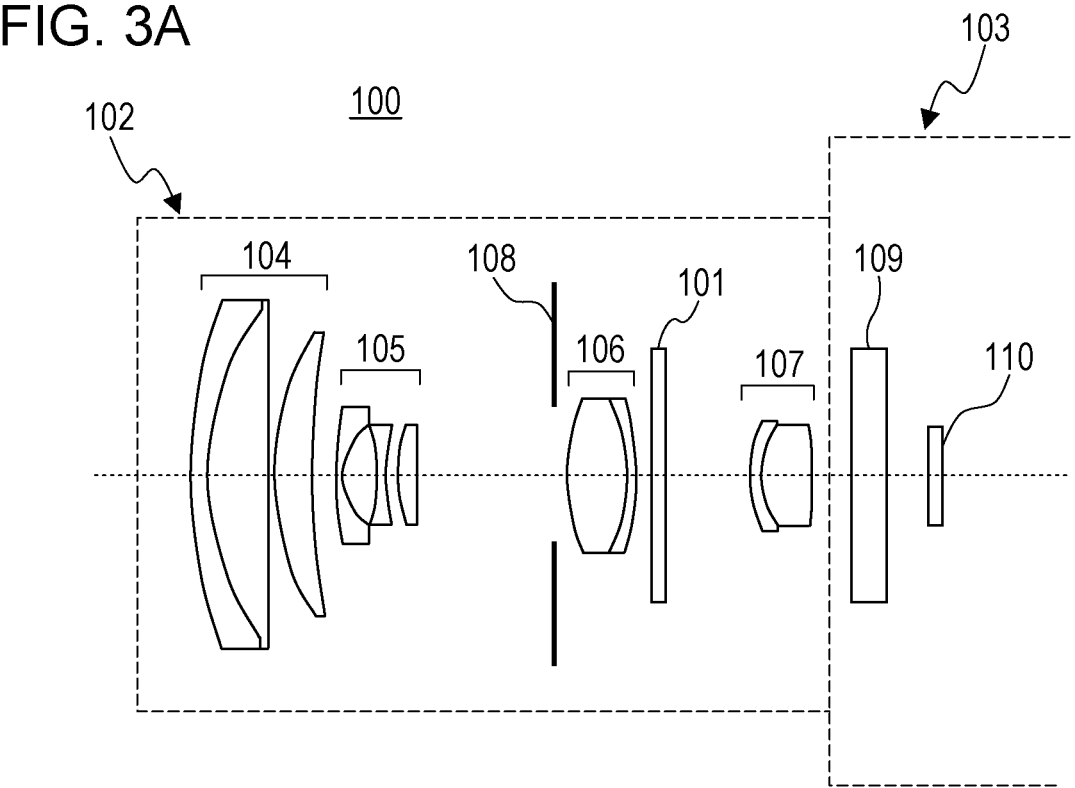
FIG. 3A is a schematic view illustrating an example of an image pickup apparatus according to an embodiment.
Figure 3B:
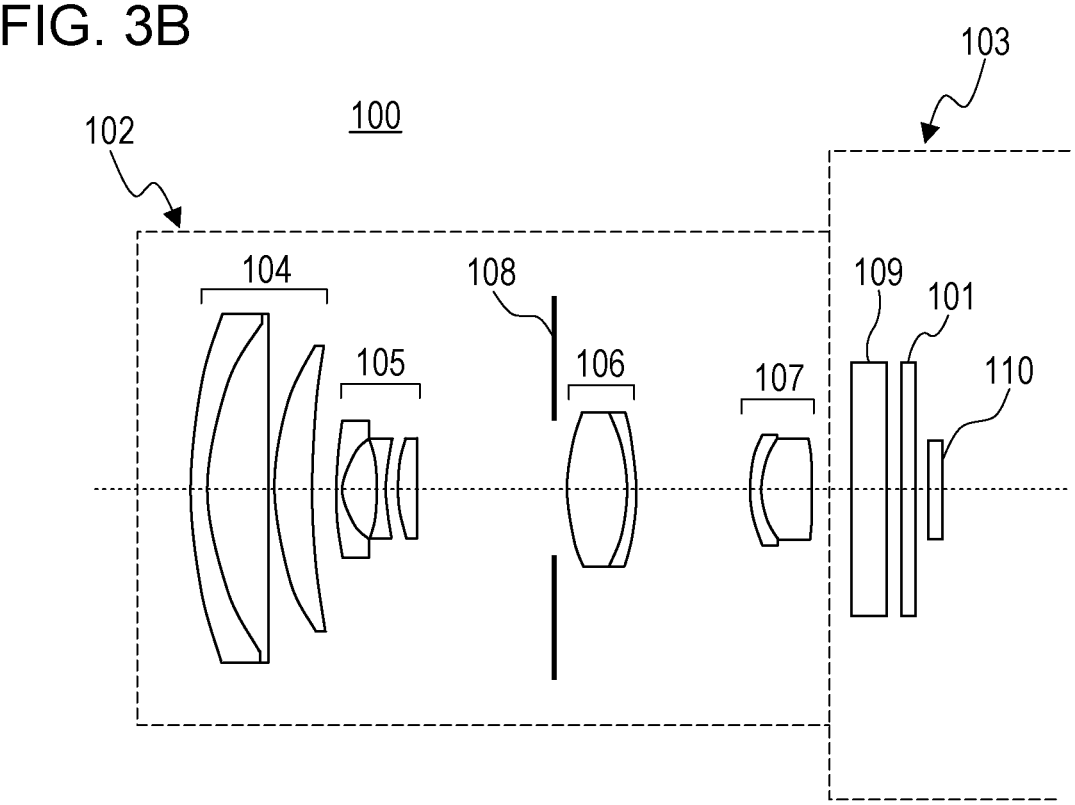
FIG. 3B is a schematic view illustrating an example of an image pickup apparatus according to an embodiment.

FIGS. 3A and 3B is a schematic view illustrating an example of the configuration of an image pickup apparatus 100 including the optical filter according to this embodiment.

The image pickup apparatus 100 is an image pickup apparatus including a lens unit 102 and an image pickup unit 103.

The lens unit 102 includes an optical filter 101, and an image pickup optical system including a plurality of lenses or lens groups. The optical filter 101 is the above-described optical filter according to this embodiment.

The lens unit 102 is, for example, in FIG. 3A, a rear-focus zoom lens performing focusing behind the stop. The lens unit 102 sequentially includes, from the object side, a first lens group 104 having a positive refractive power, a second lens group 105 having a negative refractive power, a third lens group 106 having a positive refractive power, and a fourth lens group 107 having a positive refractive power, in total, four lens groups. The distance between the second lens group 105 and the third lens group 106 is changed to achieve variable power. A portion of the lens group of the fourth lens group 107 is moved to achieve focusing.

The lens unit 102 includes, for example, an aperture stop 108 between the second lens group 105 and the third lens group 106, and the optical filter 101 between the third lens group 106 and the fourth lens group 107. The lens unit is disposed such that light passing therethrough passes through the lens groups 104 to 107, the stop 108, and the optical filter 101, and the aperture stop 108 and the optical filter 101 are used to control the amount of light.

The lens unit 102 is detachably connected, via a mount member (not shown), to the image pickup unit 103.

Incidentally, in this embodiment, the optical filter 101 is disposed between the third lens group 106 and the fourth lens group 107 within the lens unit 102; however, the image pickup apparatus 100 is not limited to this configuration. For example, the optical filter 101 may be disposed in front of the aperture stop 108 (on the subject side) or behind the aperture stop 108 (on the image pickup unit 103 side), or may be disposed in front of or behind any one of the first to fourth lens groups 104 to 107, or between lens groups. Incidentally, when the optical filter 101 is disposed at a position of focus of light, for example, a reduction in the area of the optical filter 101 is achieved, which is advantageous.

The configuration of the lens unit 102 is also not limited to the above-described configuration, and can be appropriately selected. For example, instead of the rear-focus mode, an inner-focus mode of performing focusing before the stop or another mode may be employed. In addition, instead of the zoom lens, a special lens such as a fish-eye lens or a macro lens may be appropriately selected.

The image pickup unit 103 includes a glass block 109, and a light-receiving element 110.

The glass block 109 is a glass block serving as, for example, a low-pass filter, a face plate, or a color filter.

The light-receiving element 110 is a sensor unit that receives light having passed through the lens unit, and may be, for example, a CCD or CMOS image pickup element. Alternatively, the light-receiving element 110 may be an optical sensor such as a photodiode, and an element that acquires and outputs data of the intensity or wavelength of light can be appropriately employed.

As illustrated in FIG. 3A, when the optical filter 101 is incorporated in the lens unit 102, the driving device may be disposed within the lens unit 102, or outside of the lens unit 102. When the driving device is disposed outside of the lens unit 102, the EC element 1 within the lens unit 102 and the driving device are interconnected via wiring to perform control of driving.

In the above-described configuration of the image pickup apparatus 100, the optical filter 101 is disposed within the lens unit 102. However, the present invention is not limited to this configuration; the optical filter 101 may be disposed at an appropriate position within the image pickup apparatus 100 as long as the light-receiving element 110 is disposed so as to receive light having passed through the optical filter 101.

FIG. 3B is a schematic view of an example of an image pickup apparatus in which an optical filter is disposed in the image pickup apparatus. An image pickup unit 103 includes an optical filter 101. In FIG. 3B, for example, the optical filter 101 is disposed immediately before a light-receiving element 110. When the image pickup apparatus itself includes the optical filter 101, a lens unit 102 connected thereto itself does not need to include the optical filter 101, so that an image pickup apparatus using an existing lens unit 102 can be provided so as to achieve control of light.

The image pickup apparatus 100 according to this embodiment is applicable to products including a combination of light-amount control and a light-receiving element. For example, the image pickup apparatus is applicable to cameras, digital cameras, video cameras, and digital video cameras, and is also applicable to products including image pickup apparatuses such as cellular phones, smartphones, PCs, and tablets.

Figure 4A:
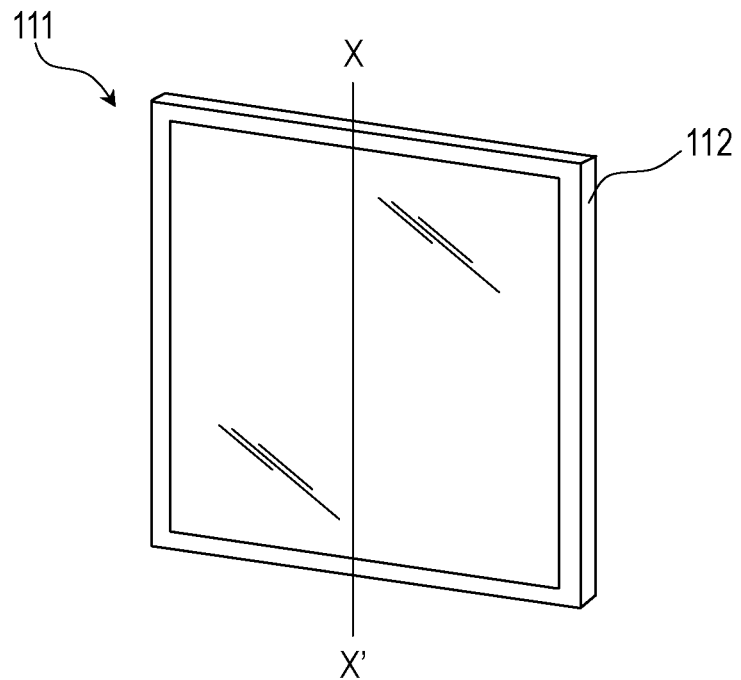
FIG. 4A is a schematic view illustrating an example of a window member according to an embodiment.
Figure 4B:
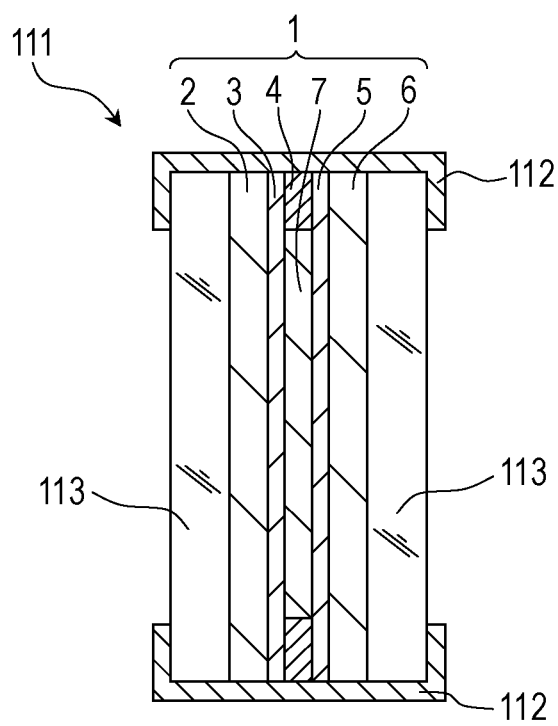
FIG. 4B is a schematic view illustrating an example of a window member according to an embodiment.

The EC element 1 according to this embodiment is also applicable to a window member. FIG. 4A is a schematic view of a window using the EC element 1 according to this embodiment. FIG. 4B is a schematic sectional view taken along line X-X in FIG. 4A.

A photochromic window 111 according to the present invention includes an EC element 1 (optical filter), transparent plates 113 sandwiching the EC element 1 therebetween, and a frame 112 surrounding the whole structure to integrate the components. The optical filter includes a driving device (not shown); the driving device may be integrated into the frame 112, or may be disposed outside of the frame 112 and connected via wiring to the EC element 1.

The transparent plates 113 are formed of a material that is not particularly limited as long as it has high light transmittance; from the viewpoint of use as a window, the material is preferably a glass material.

The material of the frame 112 is not limited, and examples include resins such as polycarbonate, acrylonitrile butadiene styrene, polyalkylene furandicarboxylate, polylactic acid, and polybutadiene terephthalate, and mixtures of the foregoing.

The frame may be any component that covers at least partially and is integrated with the optical filter.

In FIGS. 4A and 4B, the EC element 1 is a constituent component independent from the transparent plates 113; alternatively, for example, the transparent substrates 10 of the EC element 1 may be regarded as the transparent plates 113.

Such a photochromic window is applicable to, for example, control of the amount of sunlight entering a room during the day. The photochromic window is applicable to control of, in addition to the amount of sunlight, the amount of heat from the sun, to thereby control the brightness and temperature of the room. In addition, the photochromic window is applicable as a shutter in order to block line of sight from the outside to the inside of the room. Such photochromic windows are applicable to, in addition to glass windows for buildings, windows of transport such as automobiles, trains, aircraft, and ships.

Alternatively, the electrochromic element according to an embodiment of the present invention may be applied to electrochromic mirrors disposed in moving bodies such as automobiles. Such an electrochromic mirror includes a light reflection member that reflects light having transmitted the electrochromic element.

As described above, the EC element 1 including the EC layer 12 containing the organic compound represented by the general formula [1] is applicable to, for example, an optical filter, a lens unit, an image pickup apparatus, and a window member. In each of the optical filter, the lens unit, the image pickup apparatus, and the window member according to the embodiments, the organic compound represented by the general formula [1] is used alone or in combination with an EC compound that exhibits, in the colored state, absorption in a different wavelength region, to provide various absorption colors.

In the image pickup apparatus 100 according to this embodiment, the optical filter 101 is used as a photochromic component, so that the single filter enables appropriately variable control of the amount of light, which is advantageous in a reduction in the number of components and a reduction in the footprint.

EXAMPLES

Hereinafter, the present invention will be more specifically described with reference to Examples; however, the present invention is not limited to these.

Example 1

Synthesis of Example Compound A-19

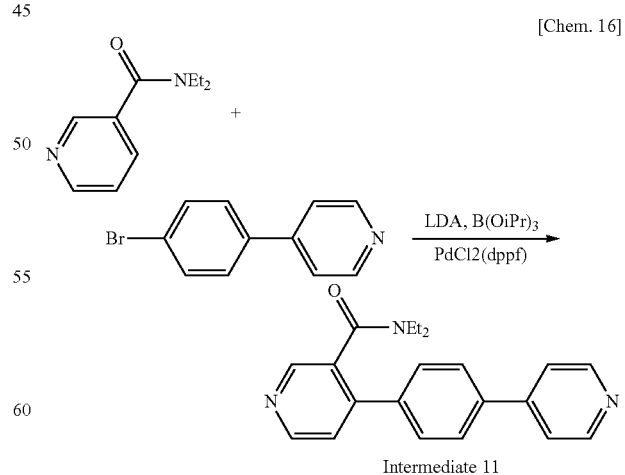

Intermediate 11

To a reaction vessel, tetrahydrofuran (8 ml) and diisopropylamine (1.6 ml, 11 mmol) were added and cooled to −70° C. To this solution, a 1.6 M butyllithium hexane solution (6.9 ml, 110 mmol) was slowly added dropwise, and subsequently heated to 0° C., to prepare a LDA solution. Separately, N,N-diethylnicotinamide (1.8 g, 10 mmol), triisopropyl borate (2.5 ml, 11 mmol), and tetrahydrofuran (8 ml) were added, and cooled to −10° C. To this solution, the LDA solution previously prepared was slowly added dropwise, and stirred at room temperature for 2 hours; subsequently, [1,1'-bis(diphenylphosphino)ferrocene]palladium (II) dichloride dichloromethane adduct (0.17 g, 0.2 mmol), 4-(4-bromophenyl)pyridine (2.58 g, 11 mmol), tetrahydrofuran (15 ml), potassium phosphate (4.1 g, 25 mmol), and water (15 ml) were added, and stirred at 60° C. for 14 hours. The reaction solution was left at room temperature, subsequently subjected to filtration through Celite, and extracted using ethyl acetate. The extract was dried over anhydrous sodium sulfate and concentrated, to obtain a brown solid. This was subjected to column purification (eluent: hexane/ethyl acetate=1/2) to obtain a yellow solid, Intermediate 11 (2.5 g, yield: 74%).

[Chem. 17]

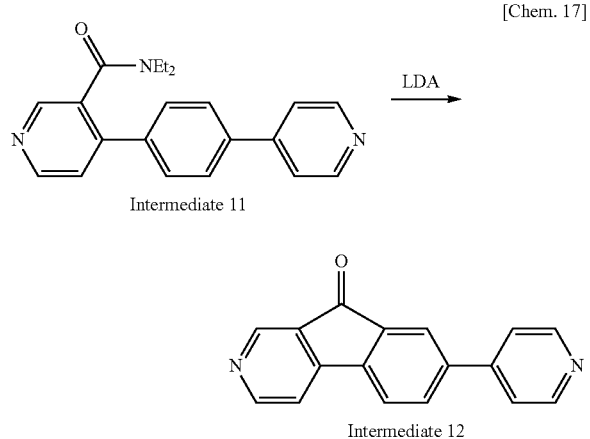

To a reaction vessel, tetrahydrofuran (8 ml) and diisopropylamine (1.3 ml, 9.1 mmol) were added and cooled to −70° C. To this solution, a 1.6 M butyllithium hexane solution (5.7 ml, 9.1 mmol) was slowly added dropwise, and subsequently heated to 0° C., to prepare a LDA solution. To this solution, a tetrahydrofuran (10 ml) solution of Intermediate 11 (2.5 g, 7.4 mmol) was slowly added dropwise, subsequently brought back to room temperature, and stirred for 16 hours. A saturated ammonium chloride solution was added, stirred for 30 minutes, and then filtered. The resultant crystals were washed sequentially with water and methanol to obtain a gray powder, Intermediate 12 (1.3 g, yield: 64%).

[Chem. 18]

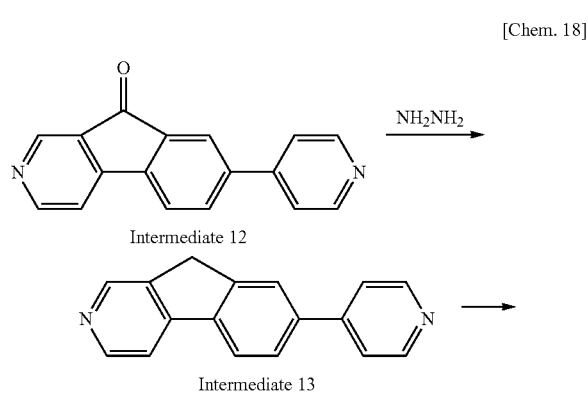

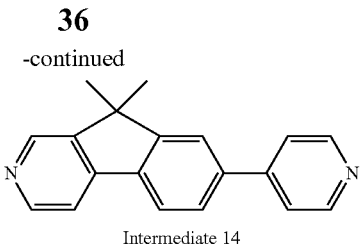

Intermediate 14

To a reaction vessel, Intermediate 12 (0.64 g, 2.5 mmol), diethylene glycol (6 mL), and hydrazine monohydrate (1.3 ml, 25 mmol) were added, and stirred under heating at 100° C. for 12 hours. This solution was left to cool, mixed with water, and then concentrated to obtain a solid. This was subjected to column purification (eluent: ethyl acetate/methanol=10/1) to obtain a pale brown solid, Intermediate 13 (0.4 g, yield: 65%).

To a reaction vessel, Intermediate 13 (0.4 g, 1.6 mmol) and N,N-dimethylformamide (5 mL) were added and cooled to 5° C. in an ice bath. To this solution, potassium tert-butoxide (0.4 g, 3.4 mmol) was added, and stirred at the same temperature for 30 minutes; subsequently, iodomethane (0.2 g, 3.4 mmol) diluted with N,N-dimethylformamide (5 mL) was added dropwise. The solution was stirred at the same temperature for 30 minutes, and then, without the cooling bath, stirred at room temperature for 3 hours. The reaction solution was mixed with a saturated aqueous sodium bicarbonate solution, and extracted with ethyl acetate; the organic layer was, sequentially washed with water and saturated brine, dried over anhydrous sodium sulfate, and concentrated to obtain a black-yellow solid. This was subjected to column purification (eluent: ethyl acetate/methanol=10/1) to obtain a beige solid, Intermediate 14 (0.17 g, yield: 39%).

[Chem. 19]

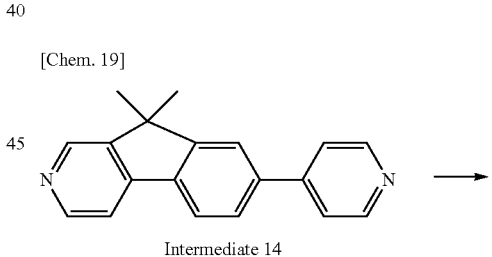

Into a reaction vessel, Intermediate 14 (0.14 g, 0.5 mmol), 2,4-dinitrobromobenzene (0.36 g, 1.5 mmol), and 10 ml of N',N', -dimethylformamide were placed into the reaction vessel, and stirred at 100° C. for 24 hours. After completion of the reaction, precipitated crystals were filtered, and washed with acetonitrile to obtain 0.29 g of Intermediate 15 (yield: 75%).

[Chem. 20]

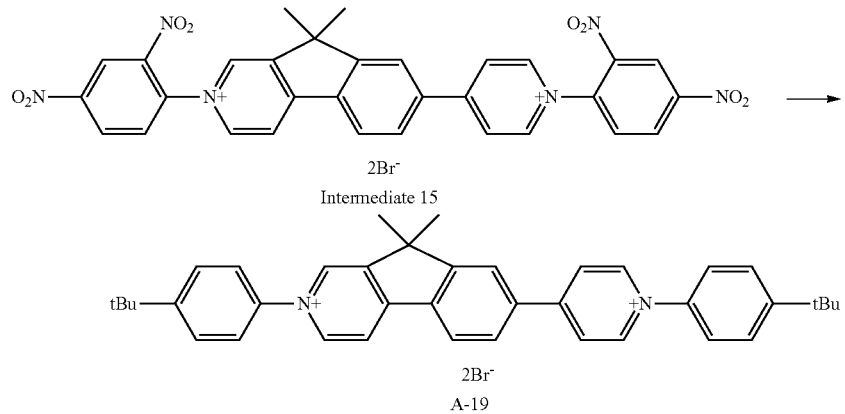

Into a reaction vessel, Intermediate 15 (0.077 g, 0.1 mmol), 4-t-butylaniline (0.045 g, 0.3 mmol), and 10 ml of ethanol were placed into the reaction vessel, and stirred while being heated to reflux for 8 hours. After the completion of the reaction, ethanol was removed in vacuo, and then ethyl acetate was added to form precipitate. The precipitate was washed with acetonitrile to obtain 0.052 g of Example compound A-19 (yield: 75%). NMR measurement was performed to examine the structure of this compound.

$^1$H NMR (CD$_3$CN, 500 MHz) σ (ppm): 9.12 (s, 1H), 9.04 (d, 2H), 8.92 (d, 1H), 8.56 (m, 3H), 8.45 (d, 1H), 8.39 (s, 1H), 8.23 (m, 1H), 7.82 (m, 4H), 7.73 (m, 4H), 1.79 (s, 6H), 1.44 (s, 9H), 1.43 (s, 9H).

Example 2

Synthesis of Example Compound A-20

Example compound A-19 (0.035 g, 0.05 mmol) was dissolved in water; an aqueous solution in which bis(trifluoromethanesulfonyl)imide lithium (0.29 g, 1 mmol) was dissolved was added dropwise, stirred at room temperature for 3 hours, and then filtered; the resultant crystals were recrystallized in ethanol, to obtain 0.051 g of Example compound A-20 (yield: 92%). NMR measurement was performed to examine the structure of this compound.

Example 3

Synthesis of Example Compound A-17

[Chem. 21]

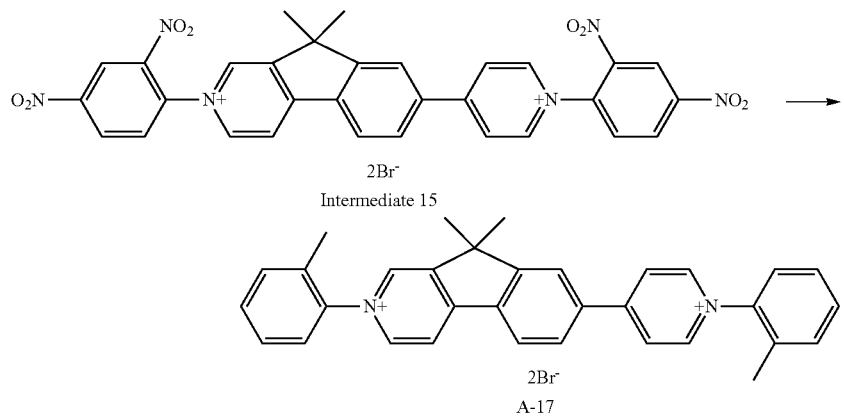

Into a reaction vessel, Intermediate 15 (0.077 g, 0.1 mmol), o-toluidine (0.064 g, 0.6 mmol), and 10 ml of ethanol were placed into the reaction vessel, and stirred while being heated to reflux for 8 hours. After the completion of the reaction, ethanol was removed in vacuo, and then ethyl acetate was added to form precipitate. The precipitate was washed with acetonitrile to obtain 0.042 g of Example compound A-17 (yield: 68%). NMR measurement was performed to examine the structure of this compound.

$^1$H NMR (DMSO-d6, 500 MHz) σ (ppm): 9.65 (s, 1H), 9.40 (d, 2H), 9.28 (d, 1H), 8.96 (d, 1H), 8.90 (d, 2H), 8.77 (s, 1H), 8.70 (d, 1H), 8.51 (d, 1H), 7.75-7.55 (m, 8H), 2.23 (s, 6H), 1.77 (s, 6H).

Example 4

Synthesis of Example Compound A-18

Example compound A-17 (0.031 g, 0.05 mmol) was dissolved in water; an aqueous solution in which bis(trifluoromethanesulfonyl)imide lithium (0.29 g, 1 mmol) was dissolved was added dropwise, stirred at room temperature for 3 hours, and then filtered. The resultant crystals were recrystallized in ethanol, to obtain 0.047 g of Example compound A-18 (yield: 92%). NMR measurement was performed to examine the structure of this compound.

$^1$H NMR (CD$_3$CN, 500 MHz) σ (ppm): 8.97 (s, 1H), 8.88 (d, 2H), 8.76 (d, 1H), 8.59 (m, 3H), 8.48 (d, 1H), 8.38 (s, 1H), 8.23 (m, 1H), 7.75-7.55 (m, 8H), 2.24 (s, 6H), 1.77 (s, 6H).

Example 5

Synthesis of Example Compound B-3

[Chem. 22]

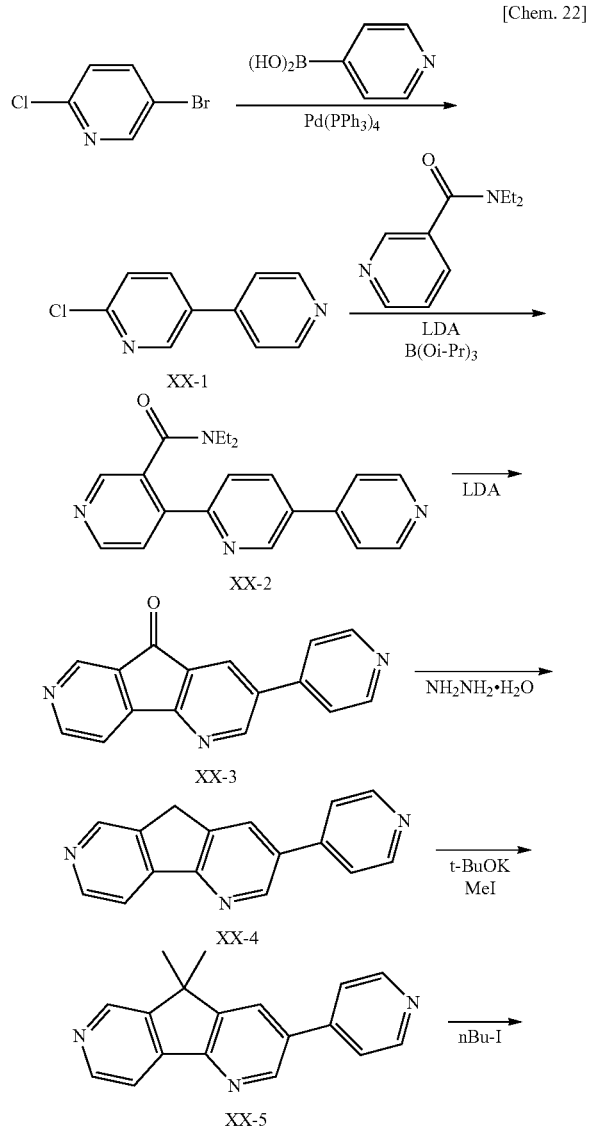

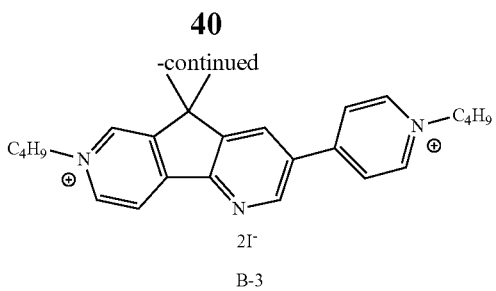

B-3

(1) Synthesis of XX-1: In a 1-L reaction vessel, 19.24 g (100 mmol) of 5-bromo-2-chloropyridine and 14.75 g (120 mmol) of 4-pyridyl boronic acid were mixed together in 1,4-dioxane/pure water (500 ml/100 ml), and nitrogen was used to replace dissolved oxygen.

Subsequently, 1.16 g (1.0 mmol) of Pd(PPh$_3$)$_4$ and 31.84 g (150 mmol) of potassium phosphate were added in a nitrogen atmosphere, and a reaction was caused at 90° C. for 17 hours.

The reaction solution was cooled to room temperature; subsequently, the aqueous layer was extracted with ethyl acetate, and silica gel chromatography (mobile phase: hexane/ethyl acetate) was performed to achieve isolation and purification, to obtain XX-1 (7.99 g, yield: 41.9%).

(2) Synthesis of XX-2: To a 50-ml reaction vessel, tetrahydrofuran (25 ml) and diisopropylamine (4.7 ml, 33 mmol) were added and cooled to −70° C. To this solution, a 1.6 M butyllithium hexane solution (21 ml, 33 mmol) was slowly added dropwise, and then heated to 0° C., to prepare a LDA solution. Separately, N,N-diethylnicotinamide (5.35 g, 30 mmol), triisopropyl borate (7.6 ml, 33 mmol), and tetrahydrofuran (25 ml) were added and cooled to −50° C. To this solution, the LDA solution previously prepared was slowly added dropwise, stirred at 0° C. for 2 hours, and subsequently concentrated under a reduced pressure. To this, XX-1 (4.72 g, 30 mmol), potassium phosphate (10.73 g, 75 mmol), and nitrogen-bubbled 1,4-dioxane/pure water (150 ml/45 ml) were added and mixed. Furthermore, tris(dibenzylideneacetone)dipalladium (550 mg, 0.6 mmol) and a 0.6 M tricyclohexylphosphine toluene solution (2.2 ml, 1.32 mmol) were added, and stirred at 90° C. for 21 hours. The reaction solution was left to cool at room temperature, then extracted with ethyl acetate, and subjected to column purification (mobile phase: hexane/ethyl acetate), to obtain a pale green solid, XX-2 (4.29 g, yield: 43%).

(3) Synthesis of XX-3: To a reaction vessel, tetrahydrofuran (15 ml) and diisopropylamine (2 ml, 14 mmol) were added, and cooled to −70° C. To this solution, a 1.6 M butyllithium hexane solution (9 ml, 13 mmol) was slowly added dropwise, and then heated to 0° C., to prepare a LDA solution. This solution was cooled to −50° C.; a tetrahydrofuran (50 ml) solution of XX-2 (4.29 g, 12.9 mmol) was slowly added dropwise, subsequently brought back to room temperature, and stirred for 4 hours. A saturated ammonium chloride solution was added, and then filtered. The resultant crystals were sequentially washed with water and methanol to obtain a pale green powder, XX-3 (2.7 g, yield: 81%).

(4) Synthesis of XX-4: To a reaction vessel, XX-3 (2.73 g, 10.5 mmol), diethylene glycol (24 mL), and hydrazine monohydrate (5.2 ml, 105 mmol) were added and stirred under heating at 150° C. for 12 hours. This solution was left to cool, and subsequently mixed with water. The precipitated solid was filtered, and washed with acetonitrile, to obtain a pale brown solid, XX-4 (1.80 g, yield: 70%).

(5) Synthesis of XX-5: To a reaction vessel, XX-4 (736 mg, 3 mmol) and N,N-dimethylformamide (10 mL) were added and cooled in an ice bath to 5° C. To this solution, potassium tert-butoxide (707 mg, 6.3 mmol) and iodomethane (0.39 ml, 6.3 mmol) were added dropwise. The solution was stirred at the same temperature for 30 minutes, and then, without the cooling bath, stirred at room temperature for 3 hours. The reaction solution was mixed with a saturated aqueous sodium bicarbonate solution, extracted with ethyl acetate, and subjected to column purification (mobile phase: hexane/ethyl acetate), to obtain a pale brown solid, XX-5 (345 mg, yield: 42%).

(6) Synthesis of B-3: To a reaction vessel, XX-5 (147 mg, 0.54 mmol), 594 mg (3.2 mmol) of 1-iodobutane, and 5 ml of acetonitrile were added, and heated to reflux at 90° C. to cause a reaction for 20 hours. After the completion of the reaction, the precipitated crystals were filtered, and washed with acetone to obtain Example compound B-3 (265 mg, yield: 76%).

Nuclear magnetic resonance spectroscopic (NMR) measurement was performed to examine the structure of the obtained compound. As a result, the obtained compound was confirmed as Example compound B-3 because the ratio of peak integral values was found to correspond to the structure. The result of the NMR spectroscopic measurement is as follows.

$^1$H NMR (DMSO-d) δ (ppm): 9.47 (s, 1H), 9.49 (d, 1H), 9.28 (d, 2H), 9.17 (d, 1H), 9.05 (d, 1H), 8.77 (d, 2H), 8.66 (d, 1H), 4.66 (t, 4H), 1.95 (m, 4H), 1.73 (s, 6H), 1.35 (m, 4H), 0.93 (t, 6H).

Example 6

Synthesis of Example Compound B4

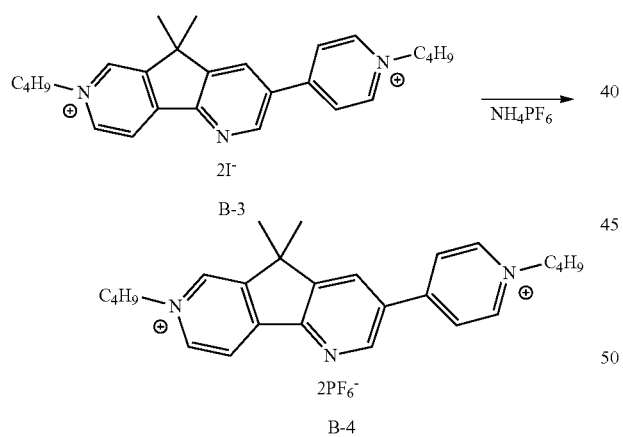

Example compound B-3 (261 mg, 0.41 mmol) was dissolved in water. An aqueous solution in which 320 mg of ammonium hexafluorophosphate was dissolved was added dropwise, and stirred at room temperature for 3 hours. The precipitated crystals were filtered, and sequentially washed with water, isopropyl alcohol, and diethyl ether, to obtain 235 mg of Example compound B-4 (yield: 85%).

NMR measurement was performed to examine the structure of this compound.

$^1$H NMR (CD$_3$CN) δ (ppm): 9.27 (d, 1H), 8.99 (s, 1H), 8.82 (d, 2H), 8.76 (d, 1H), 8.61 (d, 1H), 8.51 (d, 1H), 8.43 (d, 2H), 4.58 (t, 4H), 2.06 (m, 4H), 1.73 (s, 6H), 1.43 (m, 4H), 1.01 (t, 6H).

Example 7

Synthesis of Example Compound B-34

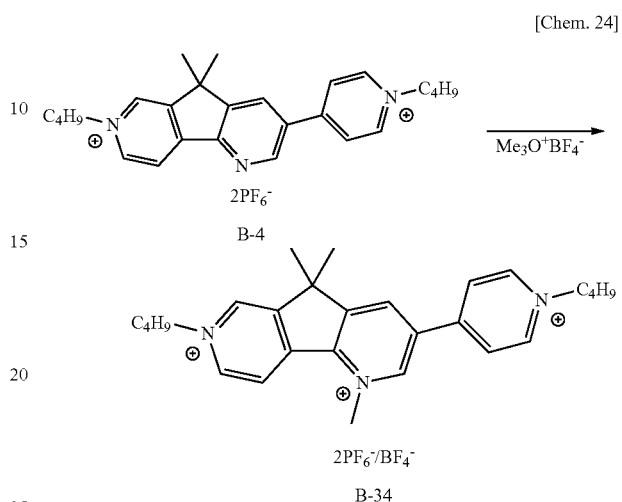

To a reaction vessel, Example compound B-4 (205 mg, 0.30 mmol) and dichloromethane (6 ml) were added, furthermore trimethyloxonium tetrafluoroborate (444 mg, 3.0 mmol) was added, and subsequently stirred at room temperature for 2 days. The precipitated solid was filtered, and sequentially washed with dichloromethane, methanol, and diethyl ether, to obtain 75 mg of Example compound B-34 (yield: 30%).

NMR measurement was performed to examine the structure of this compound.

$^1$H NMR (CD$_3$CN) δ (ppm): 9.35 (s, 1H), 9.26 (s, 2H), 9.01-8.95 (m, 3H), 8.76 (d, 1H), 8.52 (d, 2H), 4.84 (s, 3H), 4.71 (t, 2H), 4.66 (t, 2H), 2.01 (m, 4H), 1.82 (s, 6H), 1.48 (m, 4H), 1.04 (t, 6H).

Example 8

Synthesis of Example Compound B-6

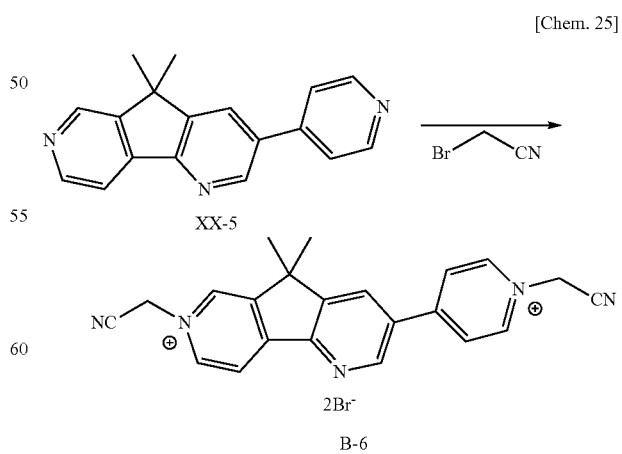

To a reaction vessel, XX-5 (104 mg, 0.38 mmol) synthesized in Example 5, bromoacetonitrile (228 mg, 1.90 mmol), and 4 ml of acetonitrile were added, and heated to reflux at 90° C. to cause a reaction for 20 hours. After the completion of the reaction, the precipitated crystals were filtered, and washed with ethyl acetate to obtain Example compound B-6 (140 mg, yield: 72%).

NMR measurement was performed to examine the structure of this compound.

$^1$H NMR (DMSO-d$_6$) δ (ppm): 9.77 (s, 1H), 9.54 (d, 1H), 9.39 (d, 2H), 9.26 (d, 1H), 9.13 (d, 1H), 8.88 (d, 2H), 8.76 (d, 1H), 6.08 (s, 2H), 6.01 (s, 2H), 1.73 (s, 6H).

Example 9

Synthesis of Example Compound B-7

[Chem. 26]

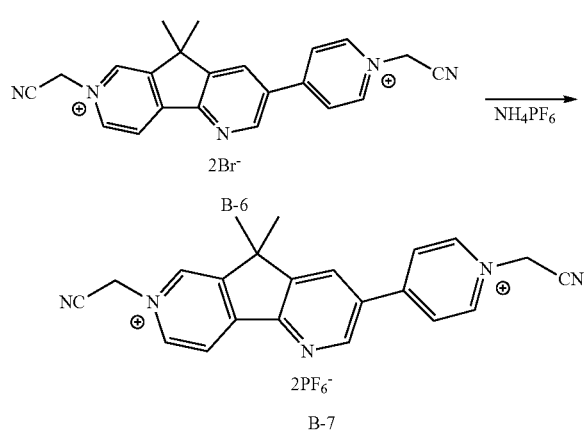

In a reaction vessel, Example compound B-6 (140 mg, 0.27 mmol) was dissolved in 10 ml of water. An aqueous solution in which 160 mg of ammonium hexafluorophosphate was dissolved was added dropwise, and stirred at room temperature for 3 hours. The precipitated crystals were filtered, and sequentially washed with water, isopropyl alcohol, and diethyl ether, to obtain 120 mg of Example compound B-7 (yield: 69%). NMR measurement was performed to examine the structure of this compound.

$^1$H NMR (CD$_3$CN) δ (ppm): 9.30 (d, 1H), 9.08 (s, 1H), 8.92 (d, 2H), 8.87 (d, 1H), 8.65 (d, 1H), 8.59 (d, 1H), 8.52 (d, 2H), 5.65 (s, 2H), 5.64 (s, 2H), 1.73 (s, 6H).

Example 10

Synthesis of Example Compound B-20

[Chem. 27]

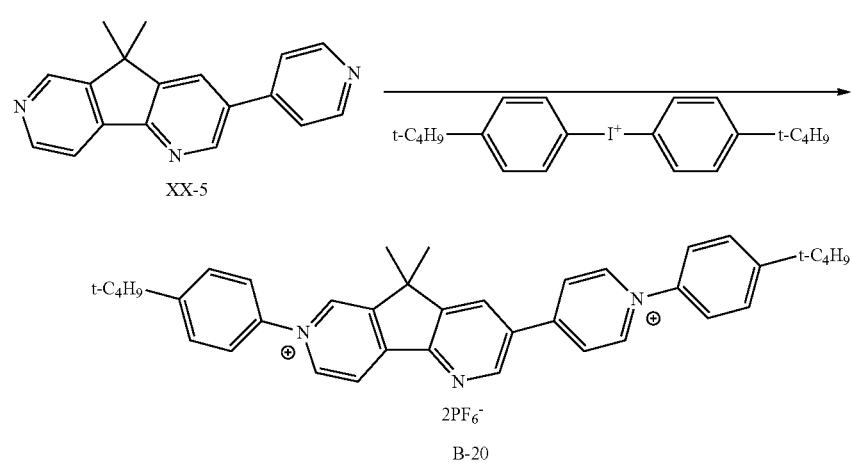

To a reaction vessel, XX-5 (150 mg, 0.55 mmol) synthesized in Example 1, bis(4-tert-butylphenyl)iodonium hexafluorophosphate (1.13 g, 2.47 mmol), copper(II) acetate monohydrate (10.0 mg, 0.055 mmol), and N,N-dimethylformamide (2.5 mL) were added and caused to react at 100° C. for 24 hours. After the completion of the reaction, the solution was concentrated under a reduced pressure, and an acetonitrile solution (5 ml) of tetrabutylammonium bromide (1 g) was added. The precipitated solid was collected by filtration, and dissolved in 10 ml of water. To this, an aqueous solution in which 220 mg of ammonium hexafluorophosphate was dissolved was added dropwise, and stirred at room temperature for 3 hours. The precipitated crystals were filtered, and sequentially washed with water, isopropyl alcohol, and diethyl ether, to obtain 290 mg of Example compound B-20 (yield: 64%).

NMR measurement was performed to examine the structure of this compound.

$^1$H NMR (CD$_3$CN) δ (ppm): 9.39 (d, 1H), 9.23 (s, 1H), 9.07 (d, 2H), 8.99 (d, 1H), 8.72 (d, 1H), 8.65 (d, 1H), 8.60 (d, 2H), 7.83-7.70 (m, 8H), 1.80 (s, 6H), 1.43 (s, 9H), 1.42 (s, 9H).

Example 11

<Production and Property Evaluation of Electrochromic Element>

As the electrolyte, tetrabutylammonium perchlorate was dissolved at a concentration of 0.1 M in propylene carbonate. Subsequently, Example compound A-20 of Example 2 was dissolved at a concentration of 40.0 mM, to obtain an EC medium.

Subsequently, on the four side regions of a pair of transparent conductive film (ITO)-equipped glass substrates, insulating layers (SiO$_2$) were formed. A PET film (manufactured by Teijin DuPont Films Japan Limited, MELINEX S (registered trademark), thickness: 125 μm) for defining the distance between the substrates was placed between the pair of transparent electrode film-equipped glass substrates. Subsequently, except for an injection port for injecting the EC medium, the substrates and the PET film were bonded together with an epoxy-based adhesive, to achieve sealing. In this way, an empty cell with an injection port was produced.

Subsequently, through the injection port, the EC medium obtained above was injected by a vacuum injection process. Subsequently, the injection port was sealed using an epoxy-based adhesive, to provide an EC element.

This EC element immediately after the production exhibited transmittances of about 80% over the entire visible-light region, and had high transparency.

Figure 5:
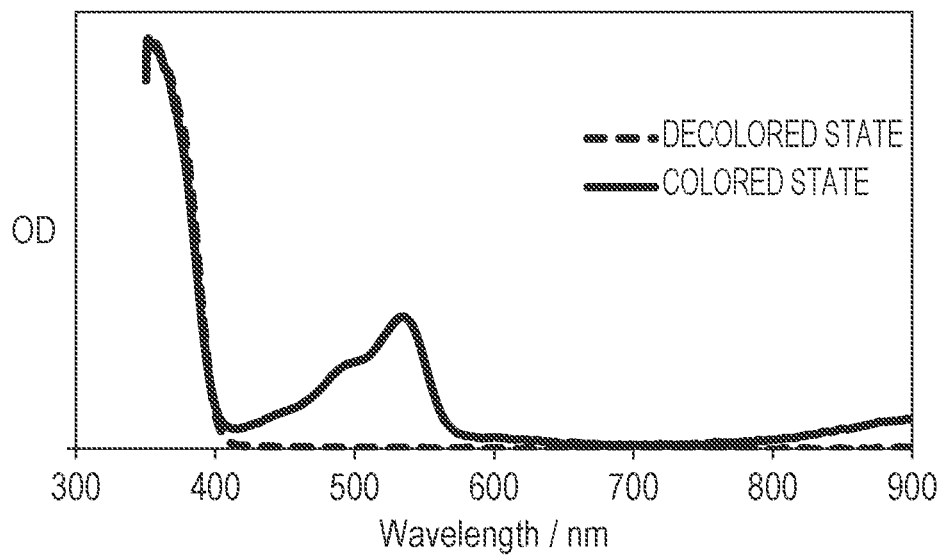
FIG. 5 is a graph illustrating transmittance spectra of Example compound A-20 in a decolored state and a colored state in Example 7.

Upon application of a voltage of 2.0 V, this element exhibited absorption (λmax=536 nm) derived from the reduction species of Example compound A-20, and the element became colored. Upon application of −0.5 V, the element became decolored. This element reversibly varies between the colored state and the decolored state. FIG. 5 illustrates ultraviolet-visible absorption spectra of the element produced in Example 10. As the light source, a DH-2000S deuterium-halogen light source manufactured by Ocean Optics, Inc. was employed.

Example 12

<Production and Property Evaluation of Electrochromic Element>

Figure 6:
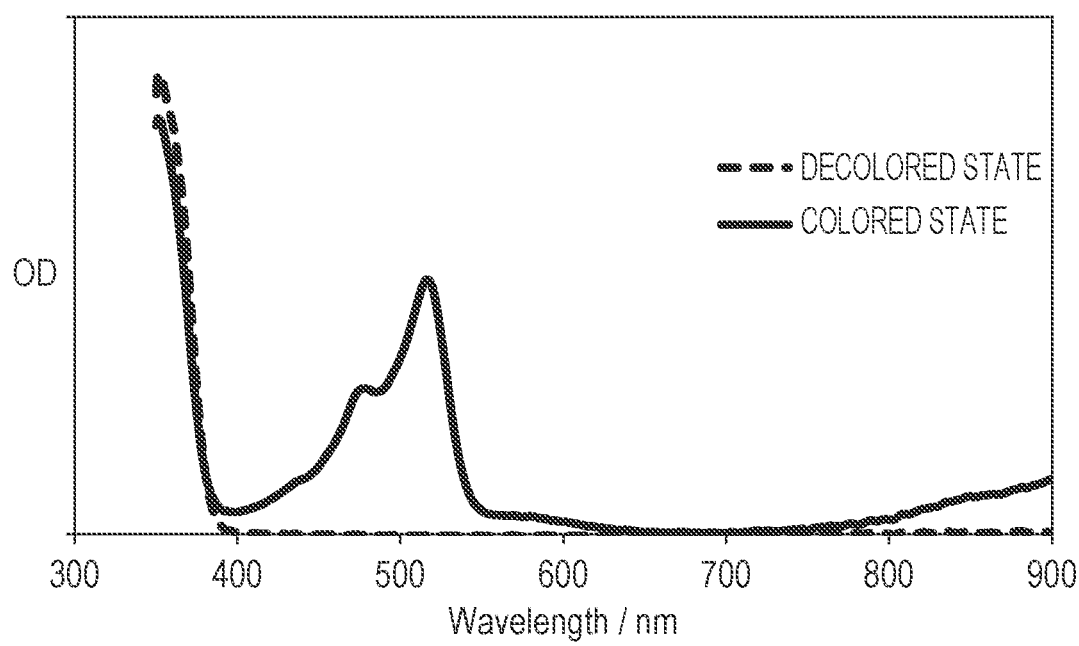
FIG. 6 illustrates ultraviolet-visible absorption spectra of an element produced in Example 11.

An element was produced by the same method as in Example 11 except that Example compound A-20 in Example 11 was replaced by Example compound A-18. Upon application of a voltage of 2.0 V, the element of this Example exhibited absorption (λmax=520 nm) derived from the reduction species of Example compound A-18, and the element became colored. Upon application of −0.5 V, the element became decolored, so that it exhibited reversible changes between the colored state and the decolored state. This element reversibly varies between the colored state and the decolored state. FIG. 6 illustrates ultraviolet-visible absorption spectra of the element produced in Example 12.

Example 13 and Comparative Example 1

<Evaluation of Electrochromic Property>

Example compound B-20 was subjected to measurement of oxidation-reduction potential, and measurement of transmittance spectra.

The measurements were performed using a solution in which Example compound B-20 was dissolved (2.0×10⁻³ mol/L) in a propylene carbonate solution (0.1 mol/L) of tetrabutylammonium hexafluorophosphate serving as a supporting electrolyte. This solution was placed in a glass cell having an optical path length of 1 mm; a mesh platinum electrode (working electrode) and a wire platinum electrode (counter electrode) were arranged, a reference electrode RE (Ag/Ag⁺) was disposed, and the measurements were performed.

The oxidation-reduction potential was measured by cyclic voltammetry (CV). Incidentally, the evaluation of reduction potential was based on measurement using ferrocene as a reference substance.

The transmittance spectrum measurement was performed by a constant potential reduction of the solution at a potential equal to or higher than the reduction potential of the compound, and using transmitted light passing through the mesh electrode. The voltage was applied using a potentiostat (CellTest 1470E) manufactured by Solartron Analytical. The spectroscopy was performed using a spectroscope (USB2000-UV-VIS) manufactured by Ocean Optics, Inc.

As a result of the CV measurement, Example compound B-20 was found to have a reduction potential of −0.99 V. The results are summarized in Table 4.

Figure 7:
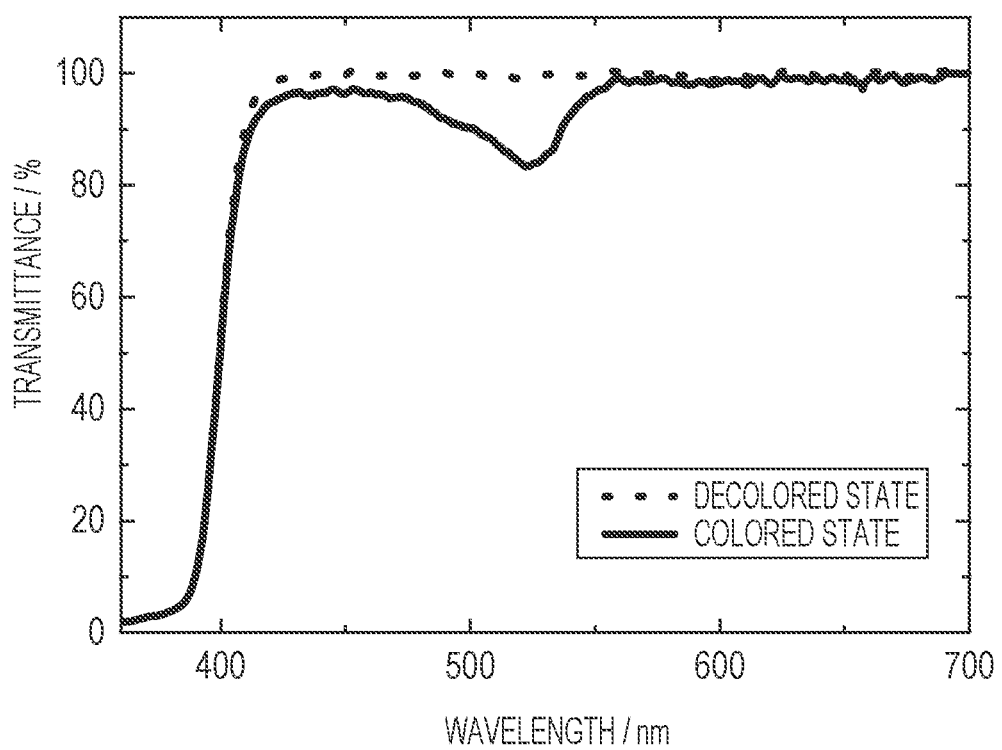
FIG. 7 illustrates transmittance spectra of Example compound B-20 in a decolored state and a colored state (reduction state).

FIG. 7 illustrates transmittance spectra of Example compound B-20 in the decolored state and the colored state (reduction state). Example compound B-20 in the decolored state does not have absorption over the entire visible-light region, and is a material having high transparency. On the other hand, the compound in the reduced and colored state has different transmittance in the visible region, and the absorption peak was at a wavelength λmax of 528 nm. This reduced and colored state returned to the colorless and transparent state due to oxidation. This has demonstrated a reversible electrochromic property due to oxidation and reduction.

Hereinafter, results of measurements using, as Comparative Example, cathodic EC compound Ref-2 will be described.

[Chem. 28]

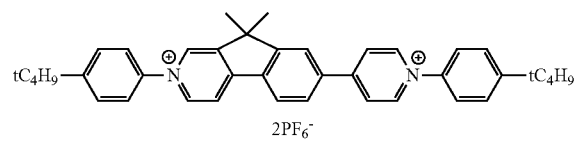

Ref-2

The cathodic EC compound Ref-2 of Reference Example is a compound having the same chemical structure as in Example compound B-20 except that the central pyridine ring is replaced by a benzene ring. Ref-2 in the reduction state exhibited, in the colored state, substantially the same absorption wavelength (λmax: ~536 nm) as in cathodic EC compound B-20; however, the reduction potential was −1.14 V, which is 150 mV lower than the reduction potential of Example compound B-20. The results are summarized in Table 4.

Example 14

<Evaluation of Electrochromic Property>

The measurements were performed as in Example 13 except that Example compound B-20 was replaced by Example compound B-7. The results are summarized in Table 4.

Example 15

<Evaluation of Electrochromic Property>

The measurements were performed as in Example 13 except that Example compound B-20 was replaced by Example compound B-34. The results are summarized in Table 4.

Example 16

<Evaluation of Electrochromic Property>

The measurements were performed as in Example 13 except that Example compound B-20 was replaced by Example compound B-4. The results are summarized in Table 4.

TABLE 4

| Compound | Absorption wavelength λmax (nm) in colored state | Reduction potential (V) |
|---|---|---|
| Comparative example compound Ref-2 | 536 | −1.14 |
| Example compound B-20 | 528 | −0.99 |
| Example compound B-7 | 510 | −0.95 |
| Example compound B-34 | 452 | −0.62 |
| Example compound B-4 | 499 | −1.15 |

Example 17

<Production and Property Evaluation of Electrochromic Element>

Example compound B-20 serving as a cathodic EC material and W-1 (5,10-diisopropyl-5,10-dihydrophenazine) having the following structure and serving as an anodic EC material were each dissolved at a concentration of 100 mM in propylene carbonate. In addition, as a thickener, polymethyl methacrylate (PMMA) was added at 5 wt %, to prepare an EC solution.

[Chem. 29]

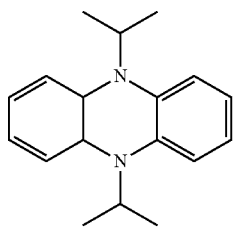

W-1

Subsequently, two transparent conductive glass plates having an indium-doped tin oxide (ITO) film were prepared, and placed such that the ITO films face each other. Subsequently, the peripheries of the two transparent conductive glass plates were bonded together using an epoxy-based sealing material containing spacer beads having a particle size of 50 m. A solution in which the anodic EC compound and the cathodic EC compound were dissolved was injected through an injection port formed in advance in the transparent conductive glass plates, to fill, with the solution, the space formed by the two transparent conductive glass plates and the sealing material. Subsequently, the injection port was sealed using an UV curable sealing agent, to obtain an EC element.

Upon application of a driving voltage of 0.9 V, this EC element exhibited an absorption (λ: ~528 nm) derived from the reduction species of Example compound B-20 and an absorption (λ: ~480 nm) derived from the oxidation species of the anodic EC compound W-1, and the EC element became colored. Upon application of 0 V, the EC element became decolored, so that it exhibited reversible changes between the colored state and the decolored state.

An organic compound according to an embodiment of the present invention is a cathodic electrochromic compound that absorbs, in the colored state, light of wavelengths of 450 to 540 nm. The organic compound is applicable to, for example, EC elements that absorb light in this region, optical filters, lens units, and image pickup apparatuses that include the EC elements.

The present invention provides a cathodic electrochromic compound that absorbs, upon coloration, light of wavelengths of 450 to 540 nm.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An organic compound represented by a general formula [1] below:

[Chem. 1]

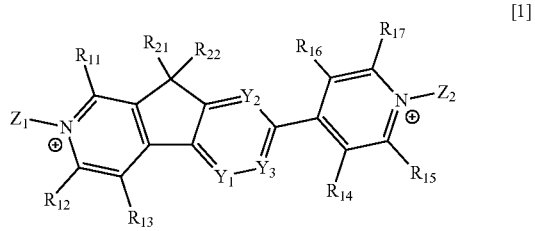

[1]

wherein, in the general formula [1], $Z_1$ and $Z_2$ are each independently selected from an alkyl group that may have a substituent, an aryl group that may have a substituent, and an aralkyl group that may have a substituent, $R_{11}$ to $R_{17}$ are each independently selected from a hydrogen atom and a substituent; the substituent is any one of an alkyl group that may have a substituent, an alkoxy group that may have a substituent, an aryl group that may have a substituent, a heterocyclic group that may have a substituent, and a halogen atom; $R_{16}$ and $R_{17}$ may be linked together to form a ring, $R_{21}$ and $R_{22}$ are each independently selected from a hydrogen atom and a substituent; the substituent is any one of an alkyl group that may have a substituent, an aryl group that may have a substituent, and an aralkyl group that may have a substituent, and $Y_1$ to $Y_3$ are each independently selected from C—H, C—CH$_3$, a N atom, and (N$^+$-L)(X$^-$) where L is any one of an alkyl group that may have a substituent, an aryl group that may have a substituent, and an aralkyl group that may have a substituent, and X$^-$ represents an anion.

2. The organic compound according to claim 1, wherein $Y_1$ to $Y_3$ are each independently selected from the group consisting of C—H and C—CH$_3$.

3. The organic compound according to claim 1, wherein $Y_1$ and $Y_2$ are each independently a N atom or (N$^+$-L)(X$^-$), and $Y_3$ is C—H or C—H$_3$.

4. The organic compound according to claim 1, wherein any one of $Y_1$ to $Y_3$ is a N atom or (N$^+$-L)(X$^-$), and other two of $Y_1$ to $Y_3$ are each independently selected from the group consisting of C—H and C—H$_3$.

5. The organic compound according to claim 1, wherein $Y_1$ is a N atom or (N$^+$-L)(X$^-$), and $Y_2$ and $Y_3$ are each independently selected from the group consisting of C—H and C—CH$_3$.

6. The organic compound according to claim 1, wherein $Z_1$ and $Z_2$ are the aryl group.

7. The organic compound according to claim 6, wherein $Z_1$ and $Z_2$ are, of the aryl group, a phenyl group, and the phenyl group has an alkyl group as a substituent.

8. The organic compound according to claim 7, wherein the alkyl group that the phenyl group has as the substituent is at a para position of a basic skeleton of the general formula [1].

9. The organic compound according to claim 7, wherein the alkyl group that the phenyl group has as the substituent is at an ortho position of a basic skeleton of the general formula [1].

10. The organic compound according to claim 8, wherein the alkyl group that the phenyl group has as the substituent is an alkyl group having 1 to 8 carbon atoms.

11. An electrochromic element comprising a pair of electrodes, and an electrochromic layer disposed between the pair of electrodes,
wherein the electrochromic layer contains the organic compound according to claim 1.

12. The electrochromic element according to claim 11, wherein the electrochromic layer further contains a second electrochromic compound different from the organic compound.

13. The electrochromic element according to claim 12, wherein the second electrochromic compound is an anodic EC compound in which a visible-light transmittance in an oxidation state is lower than a visible-light transmittance in a reduction state.

14. The electrochromic element according to claim 11, wherein the electrochromic layer contains four or more species of electrochromic compounds.

15. The electrochromic element according to claim 14, wherein the four or more species of electrochromic compounds include a viologen-based compound and a phenazine-based compound.

16. The electrochromic element according to 11, wherein the electrochromic layer is a solution layer.

17. The electrochromic element according to claim 16, wherein the electrochromic layer further contains a thickener.

18. The electrochromic element according to claim 17, wherein the thickener has a weight ratio of 20 wt % or less relative to 100 wt % of a weight of the electrochromic layer.

19. An optical filter comprising the electrochromic element according to claim 11, and an active element connected to the electrochromic element.

20. An image pickup apparatus comprising the electrochromic element according to claim 11, and a light-receiving element configured to receive light having passed through the electrochromic element.

21. A window comprising a pair of transparent substrates, the electrochromic element according to claim 11 disposed between the pair of transparent substrates, and an active element connected to the electrochromic element.

22. An electrochromic mirror comprising the electrochromic element according to claim 11, and a light reflection member including the electrochromic element on a light reflection surface.

* * * * *